(12) United States Patent
Roth et al.

(10) Patent No.: US 10,385,391 B2
(45) Date of Patent: Aug. 20, 2019

(54) ENTANGLED MATE SEQUENCING

(75) Inventors: Frederick P. Roth, Newton, MA (US); Joseph C. Mellor, Brookline, MA (US); Yong Lu, College Park, MD (US); Mark Chee, Encinitas, CA (US)

(73) Assignee: President and Fellows of Harvard College, Cambridge, MA (US)

( * ) Notice: Subject to any disclaimer, the term of this patent is extended or adjusted under 35 U.S.C. 154(b) by 176 days.

(21) Appl. No.: 13/497,069

(22) PCT Filed: Sep. 22, 2010

(86) PCT No.: PCT/US2010/049804
§ 371 (c)(1),
(2), (4) Date: Jun. 5, 2012

(87) PCT Pub. No.: WO2011/037990
PCT Pub. Date: Mar. 31, 2011

(65) Prior Publication Data
US 2012/0245039 A1 Sep. 27, 2012

Related U.S. Application Data

(60) Provisional application No. 61/244,503, filed on Sep. 22, 2009.

(51) Int. Cl.
*C40B 20/00* (2006.01)
*C12Q 1/68* (2018.01)
*C12Q 1/6874* (2018.01)

(52) U.S. Cl.
CPC .................................. *C12Q 1/6874* (2013.01)

(58) Field of Classification Search
None
See application file for complete search history.

(56) References Cited

U.S. PATENT DOCUMENTS

| | | | |
|---|---|---|---|
| 5,635,400 A | 6/1997 | Brenner | |
| 5,981,179 A | 11/1999 | Lorinez et al. | |
| 6,432,360 B1 | 8/2002 | Church | |
| 6,485,944 B1 | 11/2002 | Church et al. | |
| 6,511,803 B1 | 1/2003 | Church et al. | |
| 7,425,431 B2 | 9/2008 | Church et al. | |
| 2007/0099208 A1* | 5/2007 | Drmanac et al. | 435/6 |
| 2008/0234136 A1* | 9/2008 | Drmanac et al. | 506/3 |
| 2008/0269068 A1* | 10/2008 | Church et al. | 506/9 |
| 2009/0018024 A1 | 1/2009 | Church et al. | |
| 2009/0098555 A1 | 4/2009 | Roth et al. | |

FOREIGN PATENT DOCUMENTS

| | | |
|---|---|---|
| EP | 0799897 A1 | 8/1997 |
| WO | 2005082098 A2 | 9/2005 |
| WO | 2006073504 A2 | 7/2006 |

OTHER PUBLICATIONS

Yan et al. Nature Methods—5, 719-725 (2008).*
Smith et al. Genome Res. 2009. 19: 1836-1842.*
International Preliminary Report on Patentability for corresponding PCT/US2010/049804, dated Mar. 27, 2012.
International Search Report and Written Opinion for corresponding PCT/US2010/049804, dated Mar. 7, 2011.
Bentley, David et al., "Accurate whole human genome sequencing using reversible terminator chemistry," Nov. 2008, pp. 53-59, vol. 456, Nature.
Brenner, Charles et al., "A cultivated taste for yeast," Apr. 27, 2000, pp. 103.1-103.4, Genome Biology.
Brenner, Sydney et al., "In vitro cloning of complex mixtures of DNA on microbeads: physical separation of differently expressed cDNAs," Feb. 15, 2000, pp. 1665-1670, vol. 97, No. 4, Proceedings of the National Academy of Sciences.
Brenner, Charles, "Chemical genomics in yeast," Aug. 27, 2004, pp. 240.1-240.4, vol. 5, Issue 9, Genome Biology.
Costanzo, Michael et al., "The genetic landscape of a cell," Jan. 22, 2010, pp. 425-431, vol. 327, Science.
Eason, Robert G., "Characterization of synthetic DNA bar codes in *Saccharomyces cerevisiae* gene-deletion strains," Jul. 27, 2004, pp. 11046-11051, vol. 101, No. 30, Proceedings of the National Academy of Sciences.
Giaever, Guri et al., "Chemogenomic profiling: identifying the functional interactions of small molecules in yeast," Jan. 20, 2004, pp. 793-798, vol. 101, No. 3, Proceedings of the National Academy of Sciences.
Harris, Timothy D., "Single-molecule DNA sequencing of a viral genome," Apr. 4, 2008, pp. 106-109, vol. 320, Science.
Kircher, Martin et al., "Improved base calling for the Illumina Genome Analyzer using machine learning strategies," Aug. 14, 2009, pp. R83.1-R83.9, Genome Biology.
Kumar, Anuj et al., "Emerging technologies in yeast genomics," Apr. 2001, pp. 302-312, vol. 2, Nature Reviews.
Kwok, Pui-Yan, "High-throughput genotyping assay approaches," 2000, pp. 95-100, Pharmacogenomics.
Landegren, Ulf, et al., "Reading bits of genetic information: methods for single-nucleotide polymorphism analysis," 1998, pp. 769-776, Genome Research.
Meusnier, Isabelle, et al., "A universal DNA mini-barcode for biodiversity analysis," May 12, 2008, 4 pages, BMC Genomics.
Porreca, Gregory J., et al., "Multiplex amplification of large sets of human exons," Nov. 2007, pp. 931-936, vol. 4, No. 11, Nature Methods.
Shendure, Jay, et al., "Next-generation DNA sequencing," Oct. 2008, pp. 1135-1145, vol. 26, No. 10, Nature Biotechnology.
Shi, Michael M., "Enabling large-scale pharmacogenetic studies by high-throughput mutation detection and genotyping technologies" 2001, pp. 164-172, 47, No. 2, Clinical Chemistry.
Shoemaker, Daniel, D., "Quantitative phenotypic analysis of yeast deletion mutants using a highly parallel molecular bar-coding strategy," Dec. 14, 1996, pp. 450-456, vol. 14, Nature Genetics.
Sopko, Richelle, et al., "Linking the kinome and phosphorylome—a comprehensive review of approaches to find kinase targets," 2008, pp. 4:920-933, Molecular Biosystems.

(Continued)

*Primary Examiner* — Tracy Vivlemore
*Assistant Examiner* — Sahana S Kaup
(74) *Attorney, Agent, or Firm* — Banner & Witcoff, Ltd.

(57) ABSTRACT

Methods and compositions are provided for performing a set of N DNA sequencing reaction cycles whereby sequence information is obtained for approximately 2*N nucleotide bases.

21 Claims, 11 Drawing Sheets

Specification includes a Sequence Listing.

(56) References Cited

OTHER PUBLICATIONS

Tawfik, Dan S., et al., "Man-made cell-like compartments for molecular evolution," Jul. 1998, pp. 652-656, vol. 16, Nature Biotechnology.
Tong, Amy Hin Yan, et al., "Systematic genetic analysis with ordered arrays of yeast deletion mutants," Dec. 14, 2001, pp. 2364-2368, vol. 294, Science.
Tong, Amy Hin Yan, et al., "Global mapping of the yeast genetic interaction network," Feb. 6, 2004, pp. 808-813, vol. 303, Science.
Walhout, Albertha J. M., et al., "high-throughput yeast two-hybrid assays for large-scale protein interaction mapping," 2001, pp. 297-306, Methods.
Wang, Zhong, et al., "RNA-Seq: a revolutionary tool for transcriptomics," Jan. 2009, pp. 57-63, Nature Review Genetics.
Winzeler, Elizabeth A., et al., "Functional characterization of the *S. cerevisiae* genome by gene deletion and parallel analysis," Aug. 6, 1999, pp. 901-906, vol. 285, Science.

\* cited by examiner

A

B

C

D

B

| | |
|---|---|
| JHD2 (URA) | RTF1 |
| SWD2 (URA) | RAI1 |
| CTK2 (URA) | UBP8 |
| RTT103 (URA) | SGF73 |
| SUB2 (URA) | CHD1 |
| MTR4 (URA) | ISW1 |
| YRA2 (URA) | IOC3 |
| CTK3 (URA) | SAS5 |
| SNF6 (URA) | SAS3 |
| SWI1 (URA) | TEX1 |
| EAF6 (URA) | ADA2 |
| YRA1 (URA) | SIN3 |
| SGF29 (URA) | LDB7 |
| SGF11 (URA) | LEO1 |
| IOC4 | ITC1 |
| DST1 | SDS3 |
| RXT2 | SDC1 |
| SHG1 | CTI6 |
| THP1 | GBP2 |
| RTR1 | ASR1 |
| EAF1 | EAF3 |
| YNG1 | SAC3 |
| ECM5 | IRC20 |
| BRE1 | THP2 |
| SPT3 | SNF11 |
| SUB1 | CTK1 |
| BDF1 | ISW2 |
| RSC1 | GCN5 |
| SNF2 | JHD1 |
| HTL1 | RAD6 |
| SWI3 | YTA7 |
| SWP82 | GIS1 |
| NTO1 | BDF2 |
| RPD3 | SNF5 |
| SAS4 | PSH1 |
| TAF14 | CDC73 |
| RRP6 | |
| RTT102 | |

Figure 3 (Cont.)

SEQUENCE LISTING

<160> NUMBER OF SEQ ID NOS: 22

<210> SEQ ID NO 1
<211> LENGTH: 126
<212> TYPE: DNA
<213> ORGANISM: Artificial Sequence
<220> FEATURE:
<223> OTHER INFORMATION: Universal primer
<220> FEATURE:
<221> NAME/KEY: misc_feature
<222> LOCATION: (1)..(2)
<223> OTHER INFORMATION: wherein "n" is G or C
<220> FEATURE:
<221> NAME/KEY: misc_feature
<222> LOCATION: (3)..(3)
<223> OTHER INFORMATION: wherein "n" is C or T
<220> FEATURE:
<221> NAME/KEY: misc_feature
<222> LOCATION: (4)..(4)
<223> OTHER INFORMATION: wherein "n" is A or G
<220> FEATURE:
<221> NAME/KEY: misc_feature
<222> LOCATION: (5)..(6)
<223> OTHER INFORMATION: wherein "n" is C or T
<220> FEATURE:
<221> NAME/KEY: misc_feature
<222> LOCATION: (7)..(8)
<223> OTHER INFORMATION: wherein "n" is G or C
<220> FEATURE:
<221> NAME/KEY: misc_feature
<222> LOCATION: (9)..(10)
<223> OTHER INFORMATION: wherein "n" is C or T
<220> FEATURE:
<221> NAME/KEY: misc_feature
<222> LOCATION: (11)..(11)
<223> OTHER INFORMATION: wherein "n" is G or T
<220> FEATURE:
<221> NAME/KEY: misc_feature
<222> LOCATION: (12)..(12)
<223> OTHER INFORMATION: wherein "n" is C or T
<220> FEATURE:
<221> NAME/KEY: misc_feature
<222> LOCATION: (13)..(13)
<223> OTHER INFORMATION: wherein "n" is A or G
<220> FEATURE:
<221> NAME/KEY: misc_feature
<222> LOCATION: (14)..(14)
<223> OTHER INFORMATION: wherein "n" is G or T
<220> FEATURE:
<221> NAME/KEY: misc_feature
<222> LOCATION: (15)..(15)
<223> OTHER INFORMATION: wherein "n" is G or C
<220> FEATURE:
<221> NAME/KEY: misc_feature
<222> LOCATION: (16)..(16)
<223> OTHER INFORMATION: wherein "n" is G or T
<220> FEATURE:
<221> NAME/KEY: misc_feature
<222> LOCATION: (17)..(17)
<223> OTHER INFORMATION: wherein "n" is G or C
<220> FEATURE:
<221> NAME/KEY: misc_feature
<222> LOCATION: (18)..(19)
<223> OTHER INFORMATION: wherein "n" is A or C
<220> FEATURE:
<221> NAME/KEY: misc_feature
<222> LOCATION: (20)..(20)
<223> OTHER INFORMATION: wherein "n" is A or G
<220> FEATURE:
<221> NAME/KEY: misc_feature
<222> LOCATION: (21)..(21)
<223> OTHER INFORMATION: wherein "n" is G or C
<220> FEATURE:
<221> NAME/KEY: misc_feature
<222> LOCATION: (22)..(22)
<223> OTHER INFORMATION: wherein "n" is A or C
<220> FEATURE:
<221> NAME/KEY: misc_feature

```
<222> LOCATION: (23)..(24)
<223> OTHER INFORMATION: wherein "n" is C or T
<220> FEATURE:
<221> NAME/KEY: misc_feature
<222> LOCATION: (25)..(25)
<223> OTHER INFORMATION: wherein "n" is A or G
<220> FEATURE:
<221> NAME/KEY: misc_feature
<222> LOCATION: (26)..(26)
<223> OTHER INFORMATION: wherein "n" is C or T
<220> FEATURE:
<221> NAME/KEY: misc_feature
<222> LOCATION: (27)..(27)
<223> OTHER INFORMATION: wherein "n" is G or T
<220> FEATURE:
<221> NAME/KEY: misc_feature
<222> LOCATION: (28)..(28)
<223> OTHER INFORMATION: wherein "n" is A or G
<220> FEATURE:
<221> NAME/KEY: misc_feature
<222> LOCATION: (29)..(30)
<223> OTHER INFORMATION: wherein "n" is A or c
<220> FEATURE:
<221> NAME/KEY: misc_feature
<222> LOCATION: (31)..(35)
<223> OTHER INFORMATION: n is a, c, g, or t
<220> FEATURE:
<221> NAME/KEY: misc_feature
<222> LOCATION: (37)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t

<400> SEQUENCE: 1
cnnnnnnnnn ctnnnnnnga nnnnagngan nnnnngnnna tncggtgtcg gtctcgtagc      60
gagcacaggg agactacgtg catacccac tcccctttcg tggatgcaag agacctcgtg     120
gacatc                                                               126

<210> SEQ ID NO 2
<211> LENGTH: 40
<212> TYPE: DNA
<213> ORGANISM: Artificial Sequence
<220> FEATURE:
<223> OTHER INFORMATION: fused barcode library sequence
<220> FEATURE:
<221> NAME/KEY: misc_feature
<222> LOCATION: (1)..(1)
<223> OTHER INFORMATION: wherein "n" is G or C
<220> FEATURE:
<221> NAME/KEY: misc_feature
<222> LOCATION: (2)..(2)
<223> OTHER INFORMATION: wherein "n" is G or T
<220> FEATURE:
<221> NAME/KEY: misc_feature
<222> LOCATION: (3)..(3)
<223> OTHER INFORMATION: wherein "n" is A or T
<220> FEATURE:
<221> NAME/KEY: misc_feature
<222> LOCATION: (4)..(4)
<223> OTHER INFORMATION: wherein "n" is A or G
<220> FEATURE:
<221> NAME/KEY: misc_feature
<222> LOCATION: (5)..(5)
<223> OTHER INFORMATION: wherein "n" is C or T
<220> FEATURE:
<221> NAME/KEY: misc_feature
<222> LOCATION: (6)..(6)
<223> OTHER INFORMATION: wherein "n" is G or T
<220> FEATURE:
<221> NAME/KEY: misc_feature
<222> LOCATION: (7)..(7)
<223> OTHER INFORMATION: wherein "n" is A or G
<220> FEATURE:
```

-continued

```
<221> NAME/KEY: misc_feature
<222> LOCATION: (8)..(9)
<223> OTHER INFORMATION: wherein"n" is A or T
<220> FEATURE:
<221> NAME/KEY: misc_feature
<222> LOCATION: (10)..(11)
<223> OTHER INFORMATION: wherein"n" is G or C
<220> FEATURE:
<221> NAME/KEY: misc_feature
<222> LOCATION: (12)..(13)
<223> OTHER INFORMATION: n is a, c, g, or t
<220> FEATURE:
<221> NAME/KEY: misc_feature
<222> LOCATION: (15)..(16)
<223> OTHER INFORMATION: wherein"n" is C or T
<220> FEATURE:
<221> NAME/KEY: misc_feature
<222> LOCATION: (17)..(17)
<223> OTHER INFORMATION: wherein"n" is A or C
<220> FEATURE:
<221> NAME/KEY: misc_feature
<222> LOCATION: (18)..(18)
<223> OTHER INFORMATION: wherein"n" is A or G
<220> FEATURE:
<221> NAME/KEY: misc_feature
<222> LOCATION: (19)..(19)
<223> OTHER INFORMATION: wherein"n" is G or C
<220> FEATURE:
<221> NAME/KEY: misc_feature
<222> LOCATION: (20)..(20)
<223> OTHER INFORMATION: wherein"n" is C or T
<220> FEATURE:
<221> NAME/KEY: misc_feature
<222> LOCATION: (21)..(21)
<223> OTHER INFORMATION: wherein"n" is G or C
<220> FEATURE:
<221> NAME/KEY: misc_feature
<222> LOCATION: (22)..(22)
<223> OTHER INFORMATION: wherein"n" is A or G
<220> FEATURE:
<221> NAME/KEY: misc_feature
<222> LOCATION: (23)..(23)
<223> OTHER INFORMATION: wherein"n" is G or T
<220> FEATURE:
<221> NAME/KEY: misc_feature
<222> LOCATION: (25)..(25)
<223> OTHER INFORMATION: wherein"n" is A or T
<220> FEATURE:
<221> NAME/KEY: misc_feature
<222> LOCATION: (26)..(26)
<223> OTHER INFORMATION: wherein"n" is G or T
<220> FEATURE:
<221> NAME/KEY: misc_feature
<222> LOCATION: (27)..(27)
<223> OTHER INFORMATION: wherein"n" is A or C
<220> FEATURE:
<221> NAME/KEY: misc_feature
<222> LOCATION: (30)..(30)
<223> OTHER INFORMATION: wherein"n" is G or T
<220> FEATURE:
<221> NAME/KEY: misc_feature
<222> LOCATION: (31)..(31)
<223> OTHER INFORMATION: wherein"n" is A or G
<220> FEATURE:
<221> NAME/KEY: misc_feature
<222> LOCATION: (32)..(33)
<223> OTHER INFORMATION: wherein"n" is A or C
<220> FEATURE:
<221> NAME/KEY: misc_feature
<222> LOCATION: (35)..(35)
<223> OTHER INFORMATION: wherein"n" is C or T
<220> FEATURE:
<221> NAME/KEY: misc_feature
<222> LOCATION: (36)..(36)
<223> OTHER INFORMATION: wherein"n" is G or C
<220> FEATURE:
<221> NAME/KEY: misc_feature
<222> LOCATION: (37)..(37)
<223> OTHER INFORMATION: wherein"n" is G or T
```

-continued

```
<220> FEATURE:
<221> NAME/KEY: misc_feature
<222> LOCATION: (38)..(38)
<223> OTHER INFORMATION: wherein"n" is A or G
<220> FEATURE:
<221> NAME/KEY: misc_feature
<222> LOCATION: (40)..(40)
<223> OTHER INFORMATION: wherein"n" is A or C

<400> SEQUENCE: 2
nnnnnnngnc nnnannnnnn nnnannngan nnntnnnngn                    40

<210> SEQ ID NO 3
<211> LENGTH: 40
<212> TYPE: DNA
<213> ORGANISM: Artificial Sequence
<220> FEATURE:
<223> OTHER INFORMATION: fused barcode library sequence
<220> FEATURE:
<221> NAME/KEY: misc_feature
<222> LOCATION: (1)..(1)
<223> OTHER INFORMATION: wherein "n" is G or C
<220> FEATURE:
<221> NAME/KEY: misc_feature
<222> LOCATION: (2)..(2)
<223> OTHER INFORMATION: wherein "n" is G or T
<220> FEATURE:
<221> NAME/KEY: misc_feature
<222> LOCATION: (3)..(3)
<223> OTHER INFORMATION: wherein "n" is A or T
<220> FEATURE:
<221> NAME/KEY: misc_feature
<222> LOCATION: (4)..(4)
<223> OTHER INFORMATION: wherein "n" is A or G
<220> FEATURE:
<221> NAME/KEY: misc_feature
<222> LOCATION: (5)..(5)
<223> OTHER INFORMATION: wherein "n" is A or C
<220> FEATURE:
<221> NAME/KEY: misc_feature
<222> LOCATION: (6)..(6)
<223> OTHER INFORMATION: wherein "n" is G or T
<220> FEATURE:
<221> NAME/KEY: misc_feature
<222> LOCATION: (7)..(7)
<223> OTHER INFORMATION: wherein "n" is A or G
<220> FEATURE:
<221> NAME/KEY: misc_feature
<222> LOCATION: (9)..(9)
<223> OTHER INFORMATION: wherein "n" is G or T
<220> FEATURE:
<221> NAME/KEY: misc_feature
<222> LOCATION: (10)..(10)
<223> OTHER INFORMATION: wherein "n" is A or C
<220> FEATURE:
<221> NAME/KEY: misc_feature
<222> LOCATION: (11)..(11)
<223> OTHER INFORMATION: wherein "n" is C or T
<220> FEATURE:
<221> NAME/KEY: misc_feature
<222> LOCATION: (12)..(12)
<223> OTHER INFORMATION: wherein "n" is A or G
<220> FEATURE:
<221> NAME/KEY: misc_feature
<222> LOCATION: (14)..(14)
<223> OTHER INFORMATION: wherein "n" is A or G
<220> FEATURE:
<221> NAME/KEY: misc_feature
<222> LOCATION: (16)..(16)
<223> OTHER INFORMATION: wherein "n" is A or T
<220> FEATURE:
<221> NAME/KEY: misc_feature
<222> LOCATION: (17)..(17)
<223> OTHER INFORMATION: wherein "n" is A or C
<220> FEATURE:
<221> NAME/KEY: misc_feature
<222> LOCATION: (18)..(18)
```

```
<223> OTHER INFORMATION: wherein "n" is G or T
<220> FEATURE:
<221> NAME/KEY: misc_feature
<222> LOCATION: (20)..(20)
<223> OTHER INFORMATION: wherein "n" is C or T
<220> FEATURE:
<221> NAME/KEY: misc_feature
<222> LOCATION: (21)..(21)
<223> OTHER INFORMATION: wherein "n" is G or C
<220> FEATURE:
<221> NAME/KEY: misc_feature
<222> LOCATION: (24)..(24)
<223> OTHER INFORMATION: wherein "n" is A or C
<220> FEATURE:
<221> NAME/KEY: misc_feature
<222> LOCATION: (25)..(25)
<223> OTHER INFORMATION: wherein "n" is A or T
<220> FEATURE:
<221> NAME/KEY: misc_feature
<222> LOCATION: (26)..(26)
<223> OTHER INFORMATION: wherein "n" is G or T
<220> FEATURE:
<221> NAME/KEY: misc_feature
<222> LOCATION: (27)..(27)
<223> OTHER INFORMATION: wherein "n" is A or C
<220> FEATURE:
<221> NAME/KEY: misc_feature
<222> LOCATION: (30)..(30)
<223> OTHER INFORMATION: wherein "n" is G or T
<220> FEATURE:
<221> NAME/KEY: misc_feature
<222> LOCATION: (31)..(31)
<223> OTHER INFORMATION: wherein "n" is A or G
<220> FEATURE:
<221> NAME/KEY: misc_feature
<222> LOCATION: (32)..(32)
<223> OTHER INFORMATION: wherein "n" is A or C
<220> FEATURE:
<221> NAME/KEY: misc_feature
<222> LOCATION: (33)..(33)
<223> OTHER INFORMATION: wherein "n" is A or C
<220> FEATURE:
<221> NAME/KEY: misc_feature
<222> LOCATION: (35)..(35)
<223> OTHER INFORMATION: wherein "n" is C or T
<220> FEATURE:
<221> NAME/KEY: misc_feature
<222> LOCATION: (36)..(36)
<223> OTHER INFORMATION: wherein "n" is G or C
<220> FEATURE:
<221> NAME/KEY: misc_feature
<222> LOCATION: (37)..(37)
<223> OTHER INFORMATION: wherein "n" is G or T
<220> FEATURE:
<221> NAME/KEY: misc_feature
<222> LOCATION: (38)..(38)
<223> OTHER INFORMATION: wherein "n" is A or G
<220> FEATURE:
<221> NAME/KEY: misc_feature
<222> LOCATION: (40)..(40)
<223> OTHER INFORMATION: wherein "n" is A or C

<400> SEQUENCE: 3
nnnnnnngnn nncntnnncn natnnnngan nnntnnnngn                               40

<210> SEQ ID NO 4
<211> LENGTH: 40
<212> TYPE: DNA
<213> ORGANISM: Artificial Sequence
<220> FEATURE:
<223> OTHER INFORMATION: fused barcode library sequence
<220> FEATURE:
<221> NAME/KEY: misc_feature
<222> LOCATION: (1)..(1)
<223> OTHER INFORMATION: wherein "n" is G or C
<220> FEATURE:
<221> NAME/KEY: misc_feature
```

```
<222> LOCATION: (2)..(2)
<223> OTHER INFORMATION: wherein "n" is G or T
<220> FEATURE:
<221> NAME/KEY: misc_feature
<222> LOCATION: (3)..(3)
<223> OTHER INFORMATION: wherein "n" is A or T
<220> FEATURE:
<221> NAME/KEY: misc_feature
<222> LOCATION: (4)..(4)
<223> OTHER INFORMATION: wherein "n" is A or G
<220> FEATURE:
<221> NAME/KEY: misc_feature
<222> LOCATION: (5)..(5)
<223> OTHER INFORMATION: wherein "n" is G or C
<220> FEATURE:
<221> NAME/KEY: misc_feature
<222> LOCATION: (6)..(6)
<223> OTHER INFORMATION: wherein "n" is G or C
<220> FEATURE:
<221> NAME/KEY: misc_feature
<222> LOCATION: (8)..(8)
<223> OTHER INFORMATION: wherein "n" is G or T
<220> FEATURE:
<221> NAME/KEY: misc_feature
<222> LOCATION: (9)..(9)
<223> OTHER INFORMATION: wherein "n" is G or C
<220> FEATURE:
<221> NAME/KEY: misc_feature
<222> LOCATION: (11)..(11)
<223> OTHER INFORMATION: wherein "n" is G or T
<220> FEATURE:
<221> NAME/KEY: misc_feature
<222> LOCATION: (12)..(12)
<223> OTHER INFORMATION: wherein "n" is A or C
<220> FEATURE:
<221> NAME/KEY: misc_feature
<222> LOCATION: (13)..(13)
<223> OTHER INFORMATION: wherein "n" is G or T
<220> FEATURE:
<221> NAME/KEY: misc_feature
<222> LOCATION: (14)..(14)
<223> OTHER INFORMATION: wherein "n" is A or G
<220> FEATURE:
<221> NAME/KEY: misc_feature
<222> LOCATION: (15)..(15)
<223> OTHER INFORMATION: wherein "n" is C or T
<220> FEATURE:
<221> NAME/KEY: misc_feature
<222> LOCATION: (17)..(17)
<223> OTHER INFORMATION: wherein "n" is A or G
<220> FEATURE:
<221> NAME/KEY: misc_feature
<222> LOCATION: (18)..(18)
<223> OTHER INFORMATION: wherein "n" is G or T
<220> FEATURE:
<221> NAME/KEY: misc_feature
<222> LOCATION: (19)..(19)
<223> OTHER INFORMATION: wherein "n" is G or C
<220> FEATURE:
<221> NAME/KEY: misc_feature
<222> LOCATION: (21)..(21)
<223> OTHER INFORMATION: wherein "n" is A or G
<220> FEATURE:
<221> NAME/KEY: misc_feature
<222> LOCATION: (22)..(22)
<223> OTHER INFORMATION: wherein "n" is C or T
<220> FEATURE:
<221> NAME/KEY: misc_feature
<222> LOCATION: (23)..(23)
<223> OTHER INFORMATION: wherein "n" is G or C
<220> FEATURE:
<221> NAME/KEY: misc_feature
<222> LOCATION: (25)..(25)
<223> OTHER INFORMATION: wherein "n" is A or C
<220> FEATURE:
<221> NAME/KEY: misc_feature
<222> LOCATION: (26)..(26)
<223> OTHER INFORMATION: wherein "n" is C or T
<220> FEATURE:
```

```
<221> NAME/KEY: misc_feature
<222> LOCATION: (27)..(27)
<223> OTHER INFORMATION: wherein "n" is A or C
<220> FEATURE:
<221> NAME/KEY: misc_feature
<222> LOCATION: (30)..(30)
<223> OTHER INFORMATION: wherein "n" is G or T
<220> FEATURE:
<221> NAME/KEY: misc_feature
<222> LOCATION: (31)..(31)
<223> OTHER INFORMATION: wherein "n" is A or G
<220> FEATURE:
<221> NAME/KEY: misc_feature
<222> LOCATION: (32)..(32)
<223> OTHER INFORMATION: wherein "n" is A or C
<220> FEATURE:
<221> NAME/KEY: misc_feature
<222> LOCATION: (33)..(33)
<223> OTHER INFORMATION: wherein "n" is A or C
<220> FEATURE:
<221> NAME/KEY: misc_feature
<222> LOCATION: (35)..(35)
<223> OTHER INFORMATION: wherein "n" is C or T
<220> FEATURE:
<221> NAME/KEY: misc_feature
<222> LOCATION: (36)..(36)
<223> OTHER INFORMATION: wherein "n" is G or C
<220> FEATURE:
<221> NAME/KEY: misc_feature
<222> LOCATION: (37)..(37)
<223> OTHER INFORMATION: wherein "n" is G or T
<220> FEATURE:
<221> NAME/KEY: misc_feature
<222> LOCATION: (38)..(38)
<223> OTHER INFORMATION: wherein "n" is A or G
<220> FEATURE:
<221> NAME/KEY: misc_feature
<222> LOCATION: (40)..(40)
<223> OTHER INFORMATION: wherein "n" is A or C

<400> SEQUENCE: 4
nnnnnnanna nnnnnannna nnnannngan nnntnnnngn                           40

<210> SEQ ID NO 5
<211> LENGTH: 40
<212> TYPE: DNA
<213> ORGANISM: Artificial Sequence
<220> FEATURE:
<223> OTHER INFORMATION: fused barcode library sequence
<220> FEATURE:
<221> NAME/KEY: misc_feature
<222> LOCATION: (1)..(1)
<223> OTHER INFORMATION: wherein "n" is G or C
<220> FEATURE:
<221> NAME/KEY: misc_feature
<222> LOCATION: (2)..(2)
<223> OTHER INFORMATION: wherein "n" is G or T
<220> FEATURE:
<221> NAME/KEY: misc_feature
<222> LOCATION: (3)..(3)
<223> OTHER INFORMATION: wherein "n" is A or T
<220> FEATURE:
<221> NAME/KEY: misc_feature
<222> LOCATION: (4)..(4)
<223> OTHER INFORMATION: wherein "n" is A or G
<220> FEATURE:
<221> NAME/KEY: misc_feature
<222> LOCATION: (5)..(5)
<223> OTHER INFORMATION: wherein "n" is C or T
<220> FEATURE:
<221> NAME/KEY: misc_feature
<222> LOCATION: (6)..(6)
<223> OTHER INFORMATION: wherein "n" is G or T
<220> FEATURE:
<221> NAME/KEY: misc_feature
<222> LOCATION: (7)..(7)
<223> OTHER INFORMATION: wherein "n" is C or T
```

```
<220> FEATURE:
<221> NAME/KEY: misc_feature
<222> LOCATION: (8)..(8)
<223> OTHER INFORMATION: wherein "n" is A or T
<220> FEATURE:
<221> NAME/KEY: misc_feature
<222> LOCATION: (10)..(10)
<223> OTHER INFORMATION: wherein "n" is A or C
<220> FEATURE:
<221> NAME/KEY: misc_feature
<222> LOCATION: (12)..(12)
<223> OTHER INFORMATION: wherein "n" is A or T
<220> FEATURE:
<221> NAME/KEY: misc_feature
<222> LOCATION: (13)..(13)
<223> OTHER INFORMATION: wherein "n" is C or T
<220> FEATURE:
<221> NAME/KEY: misc_feature
<222> LOCATION: (14)..(14)
<223> OTHER INFORMATION: wherein "n" is A or T
<220> FEATURE:
<221> NAME/KEY: misc_feature
<222> LOCATION: (15)..(15)
<223> OTHER INFORMATION: wherein "n" is A or G
<220> FEATURE:
<221> NAME/KEY: misc_feature
<222> LOCATION: (16)..(16)
<223> OTHER INFORMATION: wherein "n" is A or C
<220> FEATURE:
<221> NAME/KEY: misc_feature
<222> LOCATION: (17)..(17)
<223> OTHER INFORMATION: wherein "n" is G or T
<220> FEATURE:
<221> NAME/KEY: misc_feature
<222> LOCATION: (18)..(18)
<223> OTHER INFORMATION: wherein "n" is G or C
<220> FEATURE:
<221> NAME/KEY: misc_feature
<222> LOCATION: (19)..(19)
<223> OTHER INFORMATION: wherein "n" is G or C
<220> FEATURE:
<221> NAME/KEY: misc_feature
<222> LOCATION: (20)..(20)
<223> OTHER INFORMATION: wherein "n" is G or C
<220> FEATURE:
<221> NAME/KEY: misc_feature
<222> LOCATION: (21)..(21)
<223> OTHER INFORMATION: wherein "n" is G or C
<220> FEATURE:
<221> NAME/KEY: misc_feature
<222> LOCATION: (22)..(22)
<223> OTHER INFORMATION: wherein "n" is A or T
<220> FEATURE:
<221> NAME/KEY: misc_feature
<222> LOCATION: (23)..(23)
<223> OTHER INFORMATION: wherein "n" is G or T
<220> FEATURE:
<221> NAME/KEY: misc_feature
<222> LOCATION: (25)..(25)
<223> OTHER INFORMATION: wherein "n" is A or C
<220> FEATURE:
<221> NAME/KEY: misc_feature
<222> LOCATION: (27)..(27)
<223> OTHER INFORMATION: wherein "n" is A or C
<220> FEATURE:
<221> NAME/KEY: misc_feature
<222> LOCATION: (30)..(30)
<223> OTHER INFORMATION: wherein "n" is G or T
<220> FEATURE:
<221> NAME/KEY: misc_feature
<222> LOCATION: (31)..(31)
<223> OTHER INFORMATION: wherein "n" is A or G
<220> FEATURE:
<221> NAME/KEY: misc_feature
<222> LOCATION: (32)..(32)
<223> OTHER INFORMATION: wherein "n" is A or C
<220> FEATURE:
<221> NAME/KEY: misc_feature
<222> LOCATION: (33)..(33)
```

```
<223> OTHER INFORMATION: wherein "n" is A or C
<220> FEATURE:
<221> NAME/KEY: misc_feature
<222> LOCATION: (35)..(35)
<223> OTHER INFORMATION: wherein "n" is C or T
<220> FEATURE:
<221> NAME/KEY: misc_feature
<222> LOCATION: (36)..(36)
<223> OTHER INFORMATION: wherein "n" is G or C
<220> FEATURE:
<221> NAME/KEY: misc_feature
<222> LOCATION: (37)..(37)
<223> OTHER INFORMATION: wherein "n" is G or T
<220> FEATURE:
<221> NAME/KEY: misc_feature
<222> LOCATION: (38)..(38)
<223> OTHER INFORMATION: wherein "n" is A or G
<220> FEATURE:
<221> NAME/KEY: misc_feature
<222> LOCATION: (40)..(40)
<223> OTHER INFORMATION: wherein "n" is A or C

<400> SEQUENCE: 5
nnnnnnnntn cnnnnnnnnn nnngntngan nnntnnnngn                          40

<210> SEQ ID NO 6
<211> LENGTH: 40
<212> TYPE: DNA
<213> ORGANISM: Artificial Sequence
<220> FEATURE:
<223> OTHER INFORMATION: fused barcode library sequence
<220> FEATURE:
<221> NAME/KEY: misc_feature
<222> LOCATION: (1)..(1)
<223> OTHER INFORMATION: wherein "n" is G or C
<220> FEATURE:
<221> NAME/KEY: misc_feature
<222> LOCATION: (2)..(2)
<223> OTHER INFORMATION: wherein "n" is G or T
<220> FEATURE:
<221> NAME/KEY: misc_feature
<222> LOCATION: (3)..(3)
<223> OTHER INFORMATION: wherein "n" is A or T
<220> FEATURE:
<221> NAME/KEY: misc_feature
<222> LOCATION: (4)..(4)
<223> OTHER INFORMATION: wherein "n" is A or G
<220> FEATURE:
<221> NAME/KEY: misc_feature
<222> LOCATION: (5)..(5)
<223> OTHER INFORMATION: wherein "n" is G or C
<220> FEATURE:
<221> NAME/KEY: misc_feature
<222> LOCATION: (6)..(6)
<223> OTHER INFORMATION: wherein "n" is G or C
<220> FEATURE:
<221> NAME/KEY: misc_feature
<222> LOCATION: (7)..(7)
<223> OTHER INFORMATION: wherein "n" is A or C
<220> FEATURE:
<221> NAME/KEY: misc_feature
<222> LOCATION: (11)..(11)
<223> OTHER INFORMATION: wherein "n" is A or T
<220> FEATURE:
<221> NAME/KEY: misc_feature
<222> LOCATION: (12)..(12)
<223> OTHER INFORMATION: wherein "n" is A or C
<220> FEATURE:
<221> NAME/KEY: misc_feature
<222> LOCATION: (14)..(14)
<223> OTHER INFORMATION: wherein "n" is A or G
<220> FEATURE:
<221> NAME/KEY: misc_feature
<222> LOCATION: (15)..(15)
<223> OTHER INFORMATION: wherein "n" is C or T
<220> FEATURE:
<221> NAME/KEY: misc_feature
```

```
<222> LOCATION: (16)..(16)
<223> OTHER INFORMATION: wherein "n" is A or C
<220> FEATURE:
<221> NAME/KEY: misc_feature
<222> LOCATION: (18)..(18)
<223> OTHER INFORMATION: wherein "n" is G or T
<220> FEATURE:
<221> NAME/KEY: misc_feature
<222> LOCATION: (19)..(19)
<223> OTHER INFORMATION: wherein "n" is G or C
<220> FEATURE:
<221> NAME/KEY: misc_feature
<222> LOCATION: (20)..(20)
<223> OTHER INFORMATION: wherein "n" is A or C
<220> FEATURE:
<221> NAME/KEY: misc_feature
<222> LOCATION: (21)..(21)
<223> OTHER INFORMATION: wherein "n" is G or T
<220> FEATURE:
<221> NAME/KEY: misc_feature
<222> LOCATION: (22)..(22)
<223> OTHER INFORMATION: wherein "n" is A or T
<220> FEATURE:
<221> NAME/KEY: misc_feature
<222> LOCATION: (24)..(24)
<223> OTHER INFORMATION: wherein "n" is A or T
<220> FEATURE:
<221> NAME/KEY: misc_feature
<222> LOCATION: (25)..(25)
<223> OTHER INFORMATION: wherein "n" is A or C
<220> FEATURE:
<221> NAME/KEY: misc_feature
<222> LOCATION: (26)..(26)
<223> OTHER INFORMATION: wherein "n" is G or T
<220> FEATURE:
<221> NAME/KEY: misc_feature
<222> LOCATION: (27)..(27)
<223> OTHER INFORMATION: wherein "n" is A or C
<220> FEATURE:
<221> NAME/KEY: misc_feature
<222> LOCATION: (30)..(30)
<223> OTHER INFORMATION: wherein "n" is G or T
<220> FEATURE:
<221> NAME/KEY: misc_feature
<222> LOCATION: (31)..(31)
<223> OTHER INFORMATION: wherein "n" is A or G
<220> FEATURE:
<221> NAME/KEY: misc_feature
<222> LOCATION: (32)..(32)
<223> OTHER INFORMATION: wherein "n" is A or C
<220> FEATURE:
<221> NAME/KEY: misc_feature
<222> LOCATION: (33)..(33)
<223> OTHER INFORMATION: wherein "n" is A or C
<220> FEATURE:
<221> NAME/KEY: misc_feature
<222> LOCATION: (35)..(35)
<223> OTHER INFORMATION: wherein "n" is C or T
<220> FEATURE:
<221> NAME/KEY: misc_feature
<222> LOCATION: (36)..(36)
<223> OTHER INFORMATION: wherein "n" is G or C
<220> FEATURE:
<221> NAME/KEY: misc_feature
<222> LOCATION: (37)..(37)
<223> OTHER INFORMATION: wherein "n" is G or T
<220> FEATURE:
<221> NAME/KEY: misc_feature
<222> LOCATION: (38)..(38)
<223> OTHER INFORMATION: wherein "n" is A or G
<220> FEATURE:
<221> NAME/KEY: misc_feature
<222> LOCATION: (40)..(40)
<223> OTHER INFORMATION: wherein "n" is A or C

<400> SEQUENCE: 6
nnnnnnntga nntnnnannn nngnnnngan nnntnnnngn                   40
```

```
<210> SEQ ID NO 7
<211> LENGTH: 40
<212> TYPE: DNA
<213> ORGANISM: Artificial Sequence
<220> FEATURE:
<223> OTHER INFORMATION: fused barcode library sequence
<220> FEATURE:
<221> NAME/KEY: misc_feature
<222> LOCATION: (1)..(1)
<223> OTHER INFORMATION: wherein "n" is G or C
<220> FEATURE:
<221> NAME/KEY: misc_feature
<222> LOCATION: (2)..(2)
<223> OTHER INFORMATION: wherein "n" is G or T
<220> FEATURE:
<221> NAME/KEY: misc_feature
<222> LOCATION: (3)..(3)
<223> OTHER INFORMATION: wherein "n" is A or T
<220> FEATURE:
<221> NAME/KEY: misc_feature
<222> LOCATION: (4)..(4)
<223> OTHER INFORMATION: wherein "n" is A or G
<220> FEATURE:
<221> NAME/KEY: misc_feature
<222> LOCATION: (5)..(5)
<223> OTHER INFORMATION: wherein "n" is C or T
<220> FEATURE:
<221> NAME/KEY: misc_feature
<222> LOCATION: (6)..(6)
<223> OTHER INFORMATION: wherein "n" is A or G
<220> FEATURE:
<221> NAME/KEY: misc_feature
<222> LOCATION: (8)..(8)
<223> OTHER INFORMATION: wherein "n" is A or C
<220> FEATURE:
<221> NAME/KEY: misc_feature
<222> LOCATION: (11)..(11)
<223> OTHER INFORMATION: wherein "n" is G or C
<220> FEATURE:
<221> NAME/KEY: misc_feature
<222> LOCATION: (12)..(12)
<223> OTHER INFORMATION: wherein "n" is G or C
<220> FEATURE:
<221> NAME/KEY: misc_feature
<222> LOCATION: (13)..(13)
<223> OTHER INFORMATION: wherein "n" is C or T
<220> FEATURE:
<221> NAME/KEY: misc_feature
<222> LOCATION: (14)..(14)
<223> OTHER INFORMATION: wherein "n" is G or C
<220> FEATURE:
<221> NAME/KEY: misc_feature
<222> LOCATION: (15)..(15)
<223> OTHER INFORMATION: wherein "n" is A or T
<220> FEATURE:
<221> NAME/KEY: misc_feature
<222> LOCATION: (16)..(16)
<223> OTHER INFORMATION: wherein "n" is A or T
<220> FEATURE:
<221> NAME/KEY: misc_feature
<222> LOCATION: (18)..(18)
<223> OTHER INFORMATION: wherein "n" is G or T
<220> FEATURE:
<221> NAME/KEY: misc_feature
<222> LOCATION: (20)..(20)
<223> OTHER INFORMATION: wherein "n" is G or C
<220> FEATURE:
<221> NAME/KEY: misc_feature
<222> LOCATION: (21)..(21)
<223> OTHER INFORMATION: wherein "n" is A or C
<220> FEATURE:
<221> NAME/KEY: misc_feature
<222> LOCATION: (22)..(22)
<223> OTHER INFORMATION: wherein "n" is A or C
<220> FEATURE:
<221> NAME/KEY: misc_feature
<222> LOCATION: (23)..(23)
<223> OTHER INFORMATION: wherein "n" is G or C
```

```
<220> FEATURE:
<221> NAME/KEY: misc_feature
<222> LOCATION: (24)..(24)
<223> OTHER INFORMATION: wherein "n" is A or C
<220> FEATURE:
<221> NAME/KEY: misc_feature
<222> LOCATION: (25)..(25)
<223> OTHER INFORMATION: wherein "n" is A or G
<220> FEATURE:
<221> NAME/KEY: misc_feature
<222> LOCATION: (26)..(26)
<223> OTHER INFORMATION: wherein "n" is G or T
<220> FEATURE:
<221> NAME/KEY: misc_feature
<222> LOCATION: (27)..(27)
<223> OTHER INFORMATION: wherein "n" is A or C
<220> FEATURE:
<221> NAME/KEY: misc_feature
<222> LOCATION: (30)..(30)
<223> OTHER INFORMATION: wherein "n" is G or T
<220> FEATURE:
<221> NAME/KEY: misc_feature
<222> LOCATION: (31)..(31)
<223> OTHER INFORMATION: wherein "n" is A or G
<220> FEATURE:
<221> NAME/KEY: misc_feature
<222> LOCATION: (32)..(32)
<223> OTHER INFORMATION: wherein "n" is A or C
<220> FEATURE:
<221> NAME/KEY: misc_feature
<222> LOCATION: (33)..(33)
<223> OTHER INFORMATION: wherein "n" is A or C
<220> FEATURE:
<221> NAME/KEY: misc_feature
<222> LOCATION: (35)..(35)
<223> OTHER INFORMATION: wherein "n" is C or T
<220> FEATURE:
<221> NAME/KEY: misc_feature
<222> LOCATION: (36)..(36)
<223> OTHER INFORMATION: wherein "n" is G or C
<220> FEATURE:
<221> NAME/KEY: misc_feature
<222> LOCATION: (37)..(37)
<223> OTHER INFORMATION: wherein "n" is G or T
<220> FEATURE:
<221> NAME/KEY: misc_feature
<222> LOCATION: (38)..(38)
<223> OTHER INFORMATION: wherein "n" is A or G
<220> FEATURE:
<221> NAME/KEY: misc_feature
<222> LOCATION: (40)..(40)
<223> OTHER INFORMATION: wherein "n" is A or C

<400> SEQUENCE: 7
nnnnnntntt nnnnnngncn nnnnnnngan nnntnnnngn                   40

<210> SEQ ID NO 8
<211> LENGTH: 40
<212> TYPE: DNA
<213> ORGANISM: Artificial Sequence
<220> FEATURE:
<223> OTHER INFORMATION: fused barcode library sequence
<220> FEATURE:
<221> NAME/KEY: misc_feature
<222> LOCATION: (1)..(1)
<223> OTHER INFORMATION: wherein "n" is G or C
<220> FEATURE:
<221> NAME/KEY: misc_feature
<222> LOCATION: (2)..(2)
<223> OTHER INFORMATION: wherein "n" is G or T
<220> FEATURE:
<221> NAME/KEY: misc_feature
<222> LOCATION: (3)..(3)
<223> OTHER INFORMATION: wherein "n" is A or T
<220> FEATURE:
<221> NAME/KEY: misc_feature
<222> LOCATION: (4)..(4)
```

```
<223> OTHER INFORMATION: wherein "n" is A or G
<220> FEATURE:
<221> NAME/KEY: misc_feature
<222> LOCATION: (5)..(5)
<223> OTHER INFORMATION: wherein "n" is C or T
<220> FEATURE:
<221> NAME/KEY: misc_feature
<222> LOCATION: (6)..(6)
<223> OTHER INFORMATION: wherein "n" is G or T
<220> FEATURE:
<221> NAME/KEY: misc_feature
<222> LOCATION: (7)..(7)
<223> OTHER INFORMATION: wherein "n" is A or G
<220> FEATURE:
<221> NAME/KEY: misc_feature
<222> LOCATION: (9)..(9)
<223> OTHER INFORMATION: wherein "n" is A or C
<220> FEATURE:
<221> NAME/KEY: misc_feature
<222> LOCATION: (11)..(11)
<223> OTHER INFORMATION: wherein "n" is A or T
<220> FEATURE:
<221> NAME/KEY: misc_feature
<222> LOCATION: (12)..(12)
<223> OTHER INFORMATION: wherein "n" is G or C
<220> FEATURE:
<221> NAME/KEY: misc_feature
<222> LOCATION: (13)..(13)
<223> OTHER INFORMATION: wherein "n" is G or C
<220> FEATURE:
<221> NAME/KEY: misc_feature
<222> LOCATION: (15)..(15)
<223> OTHER INFORMATION: wherein "n" is C or T
<220> FEATURE:
<221> NAME/KEY: misc_feature
<222> LOCATION: (16)..(16)
<223> OTHER INFORMATION: wherein "n" is C or T
<220> FEATURE:
<221> NAME/KEY: misc_feature
<222> LOCATION: (17)..(17)
<223> OTHER INFORMATION: wherein "n" is A or C
<220> FEATURE:
<221> NAME/KEY: misc_feature
<222> LOCATION: (18)..(18)
<223> OTHER INFORMATION: wherein "n" is A or G
<220> FEATURE:
<221> NAME/KEY: misc_feature
<222> LOCATION: (19)..(19)
<223> OTHER INFORMATION: wherein "n" is G or C
<220> FEATURE:
<221> NAME/KEY: misc_feature
<222> LOCATION: (20)..(20)
<223> OTHER INFORMATION: wherein "n" is C or T
<220> FEATURE:
<221> NAME/KEY: misc_feature
<222> LOCATION: (21)..(21)
<223> OTHER INFORMATION: wherein "n" is G or C
<220> FEATURE:
<221> NAME/KEY: misc_feature
<222> LOCATION: (22)..(22)
<223> OTHER INFORMATION: wherein "n" is A or G
<220> FEATURE:
<221> NAME/KEY: misc_feature
<222> LOCATION: (23)..(23)
<223> OTHER INFORMATION: wherein "n" is G or T
<220> FEATURE:
<221> NAME/KEY: misc_feature
<222> LOCATION: (25)..(25)
<223> OTHER INFORMATION: wherein "n" is A or T
<220> FEATURE:
<221> NAME/KEY: misc_feature
<222> LOCATION: (26)..(26)
<223> OTHER INFORMATION: wherein "n" is G or T
<220> FEATURE:
<221> NAME/KEY: misc_feature
<222> LOCATION: (27)..(27)
<223> OTHER INFORMATION: wherein "n" is A or C
<220> FEATURE:
<221> NAME/KEY: misc_feature
```

-continued

```
<222> LOCATION: (30)..(30)
<223> OTHER INFORMATION: wherein "n" is G or T
<220> FEATURE:
<221> NAME/KEY: misc_feature
<222> LOCATION: (31)..(31)
<223> OTHER INFORMATION: wherein "n" is A or G
<220> FEATURE:
<221> NAME/KEY: misc_feature
<222> LOCATION: (32)..(32)
<223> OTHER INFORMATION: wherein "n" is A or C
<220> FEATURE:
<221> NAME/KEY: misc_feature
<222> LOCATION: (33)..(33)
<223> OTHER INFORMATION: wherein "n" is A or C
<220> FEATURE:
<221> NAME/KEY: misc_feature
<222> LOCATION: (35)..(35)
<223> OTHER INFORMATION: wherein "n" is C or T
<220> FEATURE:
<221> NAME/KEY: misc_feature
<222> LOCATION: (36)..(36)
<223> OTHER INFORMATION: wherein "n" is G or C
<220> FEATURE:
<221> NAME/KEY: misc_feature
<222> LOCATION: (37)..(37)
<223> OTHER INFORMATION: wherein "n" is G or T
<220> FEATURE:
<221> NAME/KEY: misc_feature
<222> LOCATION: (38)..(38)
<223> OTHER INFORMATION: wherein "n" is A or G
<220> FEATURE:
<221> NAME/KEY: misc_feature
<222> LOCATION: (40)..(40)
<223> OTHER INFORMATION: wherein "n" is A or C

<400> SEQUENCE: 8
nnnnnnngnc nnnannnnnn nnnannngan nnntnnnngn                             40

<210> SEQ ID NO 9
<211> LENGTH: 40
<212> TYPE: DNA
<213> ORGANISM: Artificial Sequence
<220> FEATURE:
<223> OTHER INFORMATION: fused barcode library sequence
<220> FEATURE:
<221> NAME/KEY: misc_feature
<222> LOCATION: (1)..(1)
<223> OTHER INFORMATION: wherein "n" is G or C
<220> FEATURE:
<221> NAME/KEY: misc_feature
<222> LOCATION: (2)..(2)
<223> OTHER INFORMATION: wherein "n" is G or T
<220> FEATURE:
<221> NAME/KEY: misc_feature
<222> LOCATION: (3)..(3)
<223> OTHER INFORMATION: wherein "n" is A or T
<220> FEATURE:
<221> NAME/KEY: misc_feature
<222> LOCATION: (4)..(4)
<223> OTHER INFORMATION: wherein "n" is A or G
<220> FEATURE:
<221> NAME/KEY: misc_feature
<222> LOCATION: (5)..(5)
<223> OTHER INFORMATION: wherein "n" is A or C
<220> FEATURE:
<221> NAME/KEY: misc_feature
<222> LOCATION: (6)..(6)
<223> OTHER INFORMATION: wherein "n" is G or T
<220> FEATURE:
<221> NAME/KEY: misc_feature
<222> LOCATION: (7)..(7)
<223> OTHER INFORMATION: wherein "n" is A or G
<220> FEATURE:
<221> NAME/KEY: misc_feature
<222> LOCATION: (9)..(9)
<223> OTHER INFORMATION: wherein "n" is G or T
<220> FEATURE:
```

```
<221> NAME/KEY: misc_feature
<222> LOCATION: (10)..(10)
<223> OTHER INFORMATION: wherein "n" is A or C
<220> FEATURE:
<221> NAME/KEY: misc_feature
<222> LOCATION: (11)..(11)
<223> OTHER INFORMATION: wherein "n" is C or T
<220> FEATURE:
<221> NAME/KEY: misc_feature
<222> LOCATION: (12)..(12)
<223> OTHER INFORMATION: wherein "n" is A or G
<220> FEATURE:
<221> NAME/KEY: misc_feature
<222> LOCATION: (14)..(14)
<223> OTHER INFORMATION: wherein "n" is A or G
<220> FEATURE:
<221> NAME/KEY: misc_feature
<222> LOCATION: (16)..(16)
<223> OTHER INFORMATION: wherein "n" is A or T
<220> FEATURE:
<221> NAME/KEY: misc_feature
<222> LOCATION: (17)..(17)
<223> OTHER INFORMATION: wherein "n" is A or C
<220> FEATURE:
<221> NAME/KEY: misc_feature
<222> LOCATION: (18)..(18)
<223> OTHER INFORMATION: wherein "n" is G or T
<220> FEATURE:
<221> NAME/KEY: misc_feature
<222> LOCATION: (20)..(20)
<223> OTHER INFORMATION: wherein "n" is C or T
<220> FEATURE:
<221> NAME/KEY: misc_feature
<222> LOCATION: (21)..(21)
<223> OTHER INFORMATION: wherein "n" is G or C
<220> FEATURE:
<221> NAME/KEY: misc_feature
<222> LOCATION: (24)..(24)
<223> OTHER INFORMATION: wherein "n" is A or C
<220> FEATURE:
<221> NAME/KEY: misc_feature
<222> LOCATION: (25)..(25)
<223> OTHER INFORMATION: wherein "n" is A or T
<220> FEATURE:
<221> NAME/KEY: misc_feature
<222> LOCATION: (26)..(26)
<223> OTHER INFORMATION: wherein "n" is G or T
<220> FEATURE:
<221> NAME/KEY: misc_feature
<222> LOCATION: (30)..(30)
<223> OTHER INFORMATION: wherein "n" is G or T
<220> FEATURE:
<221> NAME/KEY: misc_feature
<222> LOCATION: (31)..(31)
<223> OTHER INFORMATION: wherein "n" is A or G
<220> FEATURE:
<221> NAME/KEY: misc_feature
<222> LOCATION: (32)..(32)
<223> OTHER INFORMATION: wherein "n" is A or C
<220> FEATURE:
<221> NAME/KEY: misc_feature
<222> LOCATION: (33)..(33)
<223> OTHER INFORMATION: wherein "n" is A or C
<220> FEATURE:
<221> NAME/KEY: misc_feature
<222> LOCATION: (35)..(35)
<223> OTHER INFORMATION: wherein "n" is C or T
<220> FEATURE:
<221> NAME/KEY: misc_feature
<222> LOCATION: (36)..(36)
<223> OTHER INFORMATION: wherein "n" is G or C
<220> FEATURE:
<221> NAME/KEY: misc_feature
<222> LOCATION: (37)..(37)
<223> OTHER INFORMATION: wherein "n" is G or T
<220> FEATURE:
<221> NAME/KEY: misc_feature
<222> LOCATION: (38)..(38)
<223> OTHER INFORMATION: wherein "n" is A or G
```

-continued

```
<220> FEATURE:
<221> NAME/KEY: misc_feature
<222> LOCATION: (40)..(40)
<223> OTHER INFORMATION: wherein "n" is A or CG

<400> SEQUENCE: 9
nnnnnnngnn nncntnnncn natnnnagan nnntnnnngn                              40

<210> SEQ ID NO 10
<211> LENGTH: 40
<212> TYPE: DNA
<213> ORGANISM: Artificial Sequence
<220> FEATURE:
<223> OTHER INFORMATION: fused barcode library sequence
<220> FEATURE:
<221> NAME/KEY: misc_feature
<222> LOCATION: (1)..(1)
<223> OTHER INFORMATION: wherein "n" is G or C
<220> FEATURE:
<221> NAME/KEY: misc_feature
<222> LOCATION: (2)..(2)
<223> OTHER INFORMATION: wherein "n" is G or T
<220> FEATURE:
<221> NAME/KEY: misc_feature
<222> LOCATION: (3)..(3)
<223> OTHER INFORMATION: wherein "n" is A or T
<220> FEATURE:
<221> NAME/KEY: misc_feature
<222> LOCATION: (5)..(5)
<223> OTHER INFORMATION: wherein "n" is G or C
<220> FEATURE:
<221> NAME/KEY: misc_feature
<222> LOCATION: (6)..(6)
<223> OTHER INFORMATION: wherein "n" is G or C
<220> FEATURE:
<221> NAME/KEY: misc_feature
<222> LOCATION: (8)..(8)
<223> OTHER INFORMATION: wherein "n" is G or T
<220> FEATURE:
<221> NAME/KEY: misc_feature
<222> LOCATION: (9)..(9)
<223> OTHER INFORMATION: wherein "n" is G or C
<220> FEATURE:
<221> NAME/KEY: misc_feature
<222> LOCATION: (11)..(11)
<223> OTHER INFORMATION: wherein "n" is G or T
<220> FEATURE:
<221> NAME/KEY: misc_feature
<222> LOCATION: (12)..(12)
<223> OTHER INFORMATION: wherein "n" is A or C
<220> FEATURE:
<221> NAME/KEY: misc_feature
<222> LOCATION: (13)..(13)
<223> OTHER INFORMATION: wherein "n" is G or T
<220> FEATURE:
<221> NAME/KEY: misc_feature
<222> LOCATION: (14)..(14)
<223> OTHER INFORMATION: wherein "n" is A or G
<220> FEATURE:
<221> NAME/KEY: misc_feature
<222> LOCATION: (15)..(15)
<223> OTHER INFORMATION: wherein "n" is C or T
<220> FEATURE:
<221> NAME/KEY: misc_feature
<222> LOCATION: (17)..(17)
<223> OTHER INFORMATION: wherein "n" is A or G
<220> FEATURE:
<221> NAME/KEY: misc_feature
<222> LOCATION: (18)..(18)
<223> OTHER INFORMATION: wherein "n" is G or T
<220> FEATURE:
<221> NAME/KEY: misc_feature
<222> LOCATION: (19)..(19)
<223> OTHER INFORMATION: wherein "n" is G or C
<220> FEATURE:
<221> NAME/KEY: misc_feature
<222> LOCATION: (21)..(21)
```

```
<223> OTHER INFORMATION: wherein "n" is A or G
<220> FEATURE:
<221> NAME/KEY: misc_feature
<222> LOCATION: (22)..(22)
<223> OTHER INFORMATION: wherein "n" is C or T
<220> FEATURE:
<221> NAME/KEY: misc_feature
<222> LOCATION: (23)..(23)
<223> OTHER INFORMATION: wherein "n" is G or C
<220> FEATURE:
<221> NAME/KEY: misc_feature
<222> LOCATION: (25)..(25)
<223> OTHER INFORMATION: wherein "n" is A or C
<220> FEATURE:
<221> NAME/KEY: misc_feature
<222> LOCATION: (26)..(26)
<223> OTHER INFORMATION: wherein "n" is C or T
<220> FEATURE:
<221> NAME/KEY: misc_feature
<222> LOCATION: (27)..(27)
<223> OTHER INFORMATION: wherein "n" is A or C
<220> FEATURE:
<221> NAME/KEY: misc_feature
<222> LOCATION: (30)..(30)
<223> OTHER INFORMATION: wherein "n" is G or T
<220> FEATURE:
<221> NAME/KEY: misc_feature
<222> LOCATION: (31)..(31)
<223> OTHER INFORMATION: wherein "n" is A or G
<220> FEATURE:
<221> NAME/KEY: misc_feature
<222> LOCATION: (32)..(32)
<223> OTHER INFORMATION: wherein "n" is A or C
<220> FEATURE:
<221> NAME/KEY: misc_feature
<222> LOCATION: (35)..(35)
<223> OTHER INFORMATION: wherein "n" is C or T
<220> FEATURE:
<221> NAME/KEY: misc_feature
<222> LOCATION: (36)..(36)
<223> OTHER INFORMATION: wherein "n" is G or C
<220> FEATURE:
<221> NAME/KEY: misc_feature
<222> LOCATION: (37)..(37)
<223> OTHER INFORMATION: wherein "n" is G or T
<220> FEATURE:
<221> NAME/KEY: misc_feature
<222> LOCATION: (38)..(38)
<223> OTHER INFORMATION: wherein "n" is A or G
<220> FEATURE:
<221> NAME/KEY: misc_feature
<222> LOCATION: (40)..(40)
<223> OTHER INFORMATION: wherein "n" is A or C

<400> SEQUENCE: 10
nnnannanna nnnnnannna nnnannngan nnatnnnngn                          40

<210> SEQ ID NO 11
<211> LENGTH: 40
<212> TYPE: DNA
<213> ORGANISM: Artificial Sequence
<220> FEATURE:
<223> OTHER INFORMATION: fused barcode library sequence
<220> FEATURE:
<221> NAME/KEY: misc_feature
<222> LOCATION: (1)..(1)
<223> OTHER INFORMATION: wherein "n" is G or C
<220> FEATURE:
<221> NAME/KEY: misc_feature
<222> LOCATION: (2)..(2)
<223> OTHER INFORMATION: wherein "n" is G or T
<220> FEATURE:
<221> NAME/KEY: misc_feature
<222> LOCATION: (3)..(3)
<223> OTHER INFORMATION: wherein "n" is A or T
<220> FEATURE:
<221> NAME/KEY: misc_feature
```

```
<222> LOCATION: (4)..(4)
<223> OTHER INFORMATION: wherein "n" is A or G
<220> FEATURE:
<221> NAME/KEY: misc_feature
<222> LOCATION: (5)..(5)
<223> OTHER INFORMATION: wherein "n" is A or C
<220> FEATURE:
<221> NAME/KEY: misc_feature
<222> LOCATION: (7)..(7)
<223> OTHER INFORMATION: wherein "n" is A or G
<220> FEATURE:
<221> NAME/KEY: misc_feature
<222> LOCATION: (9)..(9)
<223> OTHER INFORMATION: wherein "n" is C or T
<220> FEATURE:
<221> NAME/KEY: misc_feature
<222> LOCATION: (10)..(10)
<223> OTHER INFORMATION: wherein "n" is A or C
<220> FEATURE:
<221> NAME/KEY: misc_feature
<222> LOCATION: (11)..(11)
<223> OTHER INFORMATION: wherein "n" is G or T
<220> FEATURE:
<221> NAME/KEY: misc_feature
<222> LOCATION: (12)..(12)
<223> OTHER INFORMATION: wherein "n" is A or G
<220> FEATURE:
<221> NAME/KEY: misc_feature
<222> LOCATION: (13)..(13)
<223> OTHER INFORMATION: wherein "n" is G or C
<220> FEATURE:
<221> NAME/KEY: misc_feature
<222> LOCATION: (15)..(15)
<223> OTHER INFORMATION: wherein "n" is C or T
<220> FEATURE:
<221> NAME/KEY: misc_feature
<222> LOCATION: (16)..(16)
<223> OTHER INFORMATION: wherein "n" is A or T
<220> FEATURE:
<221> NAME/KEY: misc_feature
<222> LOCATION: (17)..(17)
<223> OTHER INFORMATION: wherein "n" is C or T
<220> FEATURE:
<221> NAME/KEY: misc_feature
<222> LOCATION: (18)..(18)
<223> OTHER INFORMATION: wherein "n" is G or T
<220> FEATURE:
<221> NAME/KEY: misc_feature
<222> LOCATION: (19)..(19)
<223> OTHER INFORMATION: wherein "n" is A or C
<220> FEATURE:
<221> NAME/KEY: misc_feature
<222> LOCATION: (21)..(21)
<223> OTHER INFORMATION: wherein "n" is G or T
<220> FEATURE:
<221> NAME/KEY: misc_feature
<222> LOCATION: (22)..(22)
<223> OTHER INFORMATION: wherein "n" is A or C
<220> FEATURE:
<221> NAME/KEY: misc_feature
<222> LOCATION: (23)..(23)
<223> OTHER INFORMATION: wherein "n" is C or T
<220> FEATURE:
<221> NAME/KEY: misc_feature
<222> LOCATION: (24)..(24)
<223> OTHER INFORMATION: wherein "n" is A or C
<220> FEATURE:
<221> NAME/KEY: misc_feature
<222> LOCATION: (25)..(25)
<223> OTHER INFORMATION: wherein "n" is A or T
<220> FEATURE:
<221> NAME/KEY: misc_feature
<222> LOCATION: (26)..(26)
<223> OTHER INFORMATION: wherein "n" is G or T
<220> FEATURE:
<221> NAME/KEY: misc_feature
<222> LOCATION: (27)..(27)
<223> OTHER INFORMATION: wherein "n" is A or C
<220> FEATURE:
```

-continued

```
<221> NAME/KEY: misc_feature
<222> LOCATION: (30)..(30)
<223> OTHER INFORMATION: wherein "n" is G or T
<220> FEATURE:
<221> NAME/KEY: misc_feature
<222> LOCATION: (31)..(31)
<223> OTHER INFORMATION: wherein "n" is A or G
<220> FEATURE:
<221> NAME/KEY: misc_feature
<222> LOCATION: (32)..(32)
<223> OTHER INFORMATION: wherein "n" is A or C
<220> FEATURE:
<221> NAME/KEY: misc_feature
<222> LOCATION: (33)..(33)
<223> OTHER INFORMATION: wherein "n" is A or C
<220> FEATURE:
<221> NAME/KEY: misc_feature
<222> LOCATION: (35)..(35)
<223> OTHER INFORMATION: wherein "n" is C or T
<220> FEATURE:
<221> NAME/KEY: misc_feature
<222> LOCATION: (36)..(36)
<223> OTHER INFORMATION: wherein "n" is G or C
<220> FEATURE:
<221> NAME/KEY: misc_feature
<222> LOCATION: (37)..(37)
<223> OTHER INFORMATION: wherein "n" is G or T
<220> FEATURE:
<221> NAME/KEY: misc_feature
<222> LOCATION: (38)..(38)
<223> OTHER INFORMATION: wherein "n" is A or G
<220> FEATURE:
<221> NAME/KEY: misc_feature
<222> LOCATION: (40)..(40)
<223> OTHER INFORMATION: wherein "n" is A or C

<400> SEQUENCE: 11
nnnnngngnn nnnannnnnt nnnnnnngan nnntnnnngn                              40

<210> SEQ ID NO 12
<211> LENGTH: 40
<212> TYPE: DNA
<213> ORGANISM: Artificial Sequence
<220> FEATURE:
<223> OTHER INFORMATION: fused barcode library sequence
<220> FEATURE:
<221> NAME/KEY: misc_feature
<222> LOCATION: (1)..(1)
<223> OTHER INFORMATION: wherein "n" is G or C
<220> FEATURE:
<221> NAME/KEY: misc_feature
<222> LOCATION: (2)..(2)
<223> OTHER INFORMATION: wherein "n" is G or T
<220> FEATURE:
<221> NAME/KEY: misc_feature
<222> LOCATION: (3)..(3)
<223> OTHER INFORMATION: wherein "n" is A or T
<220> FEATURE:
<221> NAME/KEY: misc_feature
<222> LOCATION: (4)..(4)
<223> OTHER INFORMATION: wherein "n" is A or G
<220> FEATURE:
<221> NAME/KEY: misc_feature
<222> LOCATION: (5)..(5)
<223> OTHER INFORMATION: wherein "n" is G or C
<220> FEATURE:
<221> NAME/KEY: misc_feature
<222> LOCATION: (6)..(6)
<223> OTHER INFORMATION: wherein "n" is G or C
<220> FEATURE:
<221> NAME/KEY: misc_feature
<222> LOCATION: (7)..(7)
<223> OTHER INFORMATION: wherein "n" is A or C
<220> FEATURE:
<221> NAME/KEY: misc_feature
<222> LOCATION: (11)..(11)
<223> OTHER INFORMATION: wherein "n" is A or T
```

-continued

```
<220> FEATURE:
<221> NAME/KEY: misc_feature
<222> LOCATION: (12)..(12)
<223> OTHER INFORMATION: wherein "n" is A or C
<220> FEATURE:
<221> NAME/KEY: misc_feature
<222> LOCATION: (14)..(14)
<223> OTHER INFORMATION: wherein "n" is A or G
<220> FEATURE:
<221> NAME/KEY: misc_feature
<222> LOCATION: (15)..(15)
<223> OTHER INFORMATION: wherein "n" is C or T
<220> FEATURE:
<221> NAME/KEY: misc_feature
<222> LOCATION: (16)..(16)
<223> OTHER INFORMATION: wherein "n" is A or C
<220> FEATURE:
<221> NAME/KEY: misc_feature
<222> LOCATION: (18)..(18)
<223> OTHER INFORMATION: wherein "n" is G or T
<220> FEATURE:
<221> NAME/KEY: misc_feature
<222> LOCATION: (19)..(19)
<223> OTHER INFORMATION: wherein "n" is G or C
<220> FEATURE:
<221> NAME/KEY: misc_feature
<222> LOCATION: (20)..(20)
<223> OTHER INFORMATION: wherein "n" is A or C
<220> FEATURE:
<221> NAME/KEY: misc_feature
<222> LOCATION: (21)..(21)
<223> OTHER INFORMATION: wherein "n" is G or T
<220> FEATURE:
<221> NAME/KEY: misc_feature
<222> LOCATION: (22)..(22)
<223> OTHER INFORMATION: wherein "n" is A or T
<220> FEATURE:
<221> NAME/KEY: misc_feature
<222> LOCATION: (24)..(24)
<223> OTHER INFORMATION: wherein "n" is A or T
<220> FEATURE:
<221> NAME/KEY: misc_feature
<222> LOCATION: (25)..(25)
<223> OTHER INFORMATION: wherein "n" is A or C
<220> FEATURE:
<221> NAME/KEY: misc_feature
<222> LOCATION: (26)..(26)
<223> OTHER INFORMATION: wherein "n" is G or T
<220> FEATURE:
<221> NAME/KEY: misc_feature
<222> LOCATION: (27)..(27)
<223> OTHER INFORMATION: wherein "n" is A or C
<220> FEATURE:
<221> NAME/KEY: misc_feature
<222> LOCATION: (30)..(30)
<223> OTHER INFORMATION: wherein "n" is G or T
<220> FEATURE:
<221> NAME/KEY: misc_feature
<222> LOCATION: (31)..(31)
<223> OTHER INFORMATION: wherein "n" is A or G
<220> FEATURE:
<221> NAME/KEY: misc_feature
<222> LOCATION: (32)..(32)
<223> OTHER INFORMATION: wherein "n" is A or C
<220> FEATURE:
<221> NAME/KEY: misc_feature
<222> LOCATION: (33)..(33)
<223> OTHER INFORMATION: wherein "n" is A or C
<220> FEATURE:
<221> NAME/KEY: misc_feature
<222> LOCATION: (35)..(35)
<223> OTHER INFORMATION: wherein "n" is C or T
<220> FEATURE:
<221> NAME/KEY: misc_feature
<222> LOCATION: (36)..(36)
<223> OTHER INFORMATION: wherein "n" is G or C
<220> FEATURE:
<221> NAME/KEY: misc_feature
<222> LOCATION: (37)..(37)
```

```
<223> OTHER INFORMATION: wherein "n" is G or T
<220> FEATURE:
<221> NAME/KEY: misc_feature
<222> LOCATION: (38)..(38)
<223> OTHER INFORMATION: wherein "n" is A or G
<220> FEATURE:
<221> NAME/KEY: misc_feature
<222> LOCATION: (40)..(40)
<223> OTHER INFORMATION: wherein "n" is A or C

<400> SEQUENCE: 12
nnnnnnntga nntnnnannn nngnnnngan nnntnnnngn                          40

<210> SEQ ID NO 13
<211> LENGTH: 40
<212> TYPE: DNA
<213> ORGANISM: Artificial Sequence
<220> FEATURE:
<223> OTHER INFORMATION: fused barcode library sequence
<220> FEATURE:
<221> NAME/KEY: misc_feature
<222> LOCATION: (1)..(1)
<223> OTHER INFORMATION: wherein "n" is G or C
<220> FEATURE:
<221> NAME/KEY: misc_feature
<222> LOCATION: (2)..(2)
<223> OTHER INFORMATION: wherein "n" is G or T
<220> FEATURE:
<221> NAME/KEY: misc_feature
<222> LOCATION: (3)..(3)
<223> OTHER INFORMATION: wherein "n" is A or T
<220> FEATURE:
<221> NAME/KEY: misc_feature
<222> LOCATION: (4)..(4)
<223> OTHER INFORMATION: wherein "n" is A or G
<220> FEATURE:
<221> NAME/KEY: misc_feature
<222> LOCATION: (5)..(5)
<223> OTHER INFORMATION: wherein "n" is C or T
<220> FEATURE:
<221> NAME/KEY: misc_feature
<222> LOCATION: (6)..(6)
<223> OTHER INFORMATION: wherein "n" is A or G
<220> FEATURE:
<221> NAME/KEY: misc_feature
<222> LOCATION: (8)..(8)
<223> OTHER INFORMATION: wherein "n" is A or C
<220> FEATURE:
<221> NAME/KEY: misc_feature
<222> LOCATION: (11)..(11)
<223> OTHER INFORMATION: wherein "n" is G or C
<220> FEATURE:
<221> NAME/KEY: misc_feature
<222> LOCATION: (12)..(12)
<223> OTHER INFORMATION: wherein "n" is G or C
<220> FEATURE:
<221> NAME/KEY: misc_feature
<222> LOCATION: (13)..(13)
<223> OTHER INFORMATION: wherein "n" is C or T
<220> FEATURE:
<221> NAME/KEY: misc_feature
<222> LOCATION: (14)..(14)
<223> OTHER INFORMATION: wherein "n" is G or C
<220> FEATURE:
<221> NAME/KEY: misc_feature
<222> LOCATION: (15)..(15)
<223> OTHER INFORMATION: wherein "n" is A or T
<220> FEATURE:
<221> NAME/KEY: misc_feature
<222> LOCATION: (16)..(16)
<223> OTHER INFORMATION: wherein "n" is A or T
<220> FEATURE:
<221> NAME/KEY: misc_feature
<222> LOCATION: (18)..(18)
<223> OTHER INFORMATION: wherein "n" is G or T
<220> FEATURE:
<221> NAME/KEY: misc_feature
```

```
<222> LOCATION: (20)..(20)
<223> OTHER INFORMATION: wherein "n" is G or C
<220> FEATURE:
<221> NAME/KEY: misc_feature
<222> LOCATION: (21)..(21)
<223> OTHER INFORMATION: wherein "n" is A or C
<220> FEATURE:
<221> NAME/KEY: misc_feature
<222> LOCATION: (22)..(21)
<223> OTHER INFORMATION: wherein "n" is A or C
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (23)..(23)
<223> OTHER INFORMATION: wherein "n" is G or C
<220> FEATURE:
<221> NAME/KEY: misc_feature
<222> LOCATION: (24)..(24)
<223> OTHER INFORMATION: wherein "n" is A or C
<220> FEATURE:
<221> NAME/KEY: misc_feature
<222> LOCATION: (25)..(25)
<223> OTHER INFORMATION: wherein "n" is A or G
<220> FEATURE:
<221> NAME/KEY: misc_feature
<222> LOCATION: (26)..(26)
<223> OTHER INFORMATION: wherein "n" is G or T
<220> FEATURE:
<221> NAME/KEY: misc_feature
<222> LOCATION: (30)..(30)
<223> OTHER INFORMATION: wherein "n" is G or T
<220> FEATURE:
<221> NAME/KEY: misc_feature
<222> LOCATION: (31)..(31)
<223> OTHER INFORMATION: wherein "n" is A or G
<220> FEATURE:
<221> NAME/KEY: misc_feature
<222> LOCATION: (32)..(32)
<223> OTHER INFORMATION: wherein "n" is A or C
<220> FEATURE:
<221> NAME/KEY: misc_feature
<222> LOCATION: (33)..(33)
<223> OTHER INFORMATION: wherein "n" is A or C
<220> FEATURE:
<221> NAME/KEY: misc_feature
<222> LOCATION: (36)..(36)
<223> OTHER INFORMATION: wherein "n" is G or C
<220> FEATURE:
<221> NAME/KEY: misc_feature
<222> LOCATION: (37)..(37)
<223> OTHER INFORMATION: wherein "n" is G or T
<220> FEATURE:
<221> NAME/KEY: misc_feature
<222> LOCATION: (38)..(38)
<223> OTHER INFORMATION: wherein "n" is A or G
<220> FEATURE:
<221> NAME/KEY: misc_feature
<222> LOCATION: (40)..(40)
<223> OTHER INFORMATION: wherein "n" is A or C

<400> SEQUENCE: 13
nnnnnntntt nnnnnngncn nnnnnnagan nnntynnngn                         40

<210> SEQ ID NO 14
<211> LENGTH: 33
<212> TYPE: DNA
<213> ORGANISM: Artificial Sequence
<220> FEATURE:
<223> OTHER INFORMATION: construction oligonucleotide sequence

<400> SEQUENCE: 14
acactctttc cctacacgac gctcttccga tct                                33
```

<210> SEQ ID NO 15
<211> LENGTH: 32
<212> TYPE: DNA
<213> ORGANISM: Artificial Sequence
<220> FEATURE:
<223> OTHER INFORMATION: construction oligonucleotide sequence
<220> FEATURE:
<221> NAME/KEY: misc_feature
<222> LOCATION: (1)..(1)
<223> OTHER INFORMATION: 5' phosphorylation

<400> SEQUENCE: 15
gatcggaaga gcgcgtcagt caccggagcc ac                          32

<210> SEQ ID NO 16
<211> LENGTH: 33
<212> TYPE: DNA
<213> ORGANISM: Artificial Sequence
<220> FEATURE:
<223> OTHER INFORMATION: construction oligonucleotide sequence

<400> SEQUENCE: 16
gagccgtaag gacgacttgg atgctggacc tgt                         33

<210> SEQ ID NO 17
<211> LENGTH: 32
<212> TYPE: DNA
<213> ORGANISM: Artificial Sequence
<220> FEATURE:
<223> OTHER INFORMATION: construction oligonucleotide sequence
<220> FEATURE:
<221> NAME/KEY: misc_feature
<222> LOCATION: (1)..(1)
<223> OTHER INFORMATION: 5' phosphorylation

<400> SEQUENCE: 17
caggtccagc atcgtggctc cggtgactga cg                          32

<210> SEQ ID NO 18
<211> LENGTH: 58
<212> TYPE: DNA
<213> ORGANISM: Artificial Sequence
<220> FEATURE:
<223> OTHER INFORMATION: construction oligonucleotide sequence

<400> SEQUENCE: 18
aatgatacgg cgaccaccga gatctacact ctttccctac acgacgctct tccgatct     58

<210> SEQ ID NO 19
<211> LENGTH: 44
<212> TYPE: DNA
<213> ORGANISM: Artificial Sequence
<220> FEATURE:
<223> OTHER INFORMATION: construction oligonucleotide sequence

<400> SEQUENCE: 19
caagcagaag acggcatacg agatgagccg taaggacgac ttgg             44

<210> SEQ ID NO 20
<211> LENGTH: 162
<212> TYPE: DNA
<213> ORGANISM: Artificial Sequence
<220> FEATURE:
<223> OTHER INFORMATION: PCR primer

<400> SEQUENCE: 20
aatgatacgg cgaccaccga gatctacact ctttccctac acgacgctct tccgatctag    60

```
atcggaagag cgcgtcagtc accggagcca cgatgctgga cctgtaaagg tccagcatcc      120
aagtcgtcct tacggctcat ctcgtatgcc gtcttctgct tg                          162

<210> SEQ ID NO 21
<211> LENGTH: 36
<212> TYPE: DNA
<213> ORGANISM: Artificial Sequence
<220> FEATURE:
<223> OTHER INFORMATION: sequencing primer

<400> SEQUENCE: 21
tctacactct ttccctacac gacgctcttc cgatct                                 36

<210> SEQ ID NO 22
<211> LENGTH: 35
<212> TYPE: DNA
<213> ORGANISM: Artificial Sequence
<220> FEATURE:
<223> OTHER INFORMATION: sequencing primer

<400> SEQUENCE: 22
gaagagcgcg tcagtcaccg gagccacgat gctgg                                  35
```

ENTANGLED MATE SEQUENCING

RELATED APPLICATION DATA

This application is a National Stage Application under 35 U.S.C. 371 of co-pending PCT Application PCT/US2010/049804 designating the United States and filed Sep. 22, 2010; which claims priority to U.S. Provisional Patent Application No. 61/244,503, filed on Sep. 22, 2009 each of which are hereby incorporated by reference in their entireties.

STATEMENT OF GOVERNMENT INTERESTS

This invention was made with Government support under HG004756 and HG003224 awarded by the National Institutes of Health. The Government has certain rights in the invention.

BACKGROUND

DNA sequencing using primer-directed, dye-based termination, reversible termination, sequence-specific single-strand DNA ligation, or other sequencing protocols known in the art typically results in obtaining the informational equivalent of a single nucleotide base from a given template sequence from each reaction cycle of sequencing chemistry. The widely used capillary-based Sanger sequencing method, for example, uses a mixture of four fluorescent dideoxy terminator nucleotides per cycle to determine which of four nucleotides occurs at a given sequence position. Sequencing reactions are typically initiated by use of a priming sequence that flanks a DNA template region of interest in a given DNA clone, with the typical restriction that a single template region is sequenced. The sequence information obtained from a single conventional read provides 2 bits of information (I) per reaction cycle ($I=\Sigma-pi \log 2 (pi)$), where the sum is over each possible nucleotide and pi is the a priori probability of observing any given nucleotide which is equal to 25% if all four nucleotides are equally likely a priori).

SUMMARY

When two template sequences are sequenced in the same reaction (for example, using either using a single primer directed to two identical priming sites, or using a mixture of two primers directed at two different priming sites) an increased amount of information is gathered about two sequence templates simultaneously, at the cost of lost information regarding which template region produced which signal. The two signals are therefore referred to as "entangled."

The theoretical properties of entangled sequencing data can be considered in the following manner. If only a single base (e.g. "A") is observed at a given cycle from co-located, synchronously-primed sequencing reactions, this base must be present at the position corresponding to that cycle in both templates (i.e., both have "A" at position one). Such cycles, which occur approximately 25% of the time in sequences having uniform nucleotide composition, will yield four bits of information. If a mixture of two bases is observed (e.g., "A" and "C"), however, one bit of information is lost by not knowing which template sequence contains which base. Three bits of information are gained from such cycles ($I=4-\Sigma-p_i \log_2 (p_i)$) where the sum is over the two remaining possible nucleotides, and $p_i$ is 50% for each of the two possible nucleotides), which should occur 75% of the time.

The resulting averaged expectation of 3.25 bits of information per cycle corresponds to a 62.5% increase in information compared with sequencing one template alone. The amount of information revealed can vary when the four bases are not equally likely a priori in each sequence, but is generally higher for entangled mate sequencing under a wide range of circumstances.

Methods of sequencing entangled sequences are provided that allow for simultaneous reading of two or more sequence regions on template DNA fragments (e.g., from a clonal population of DNA). In certain aspects, nucleotide sequences of two or more tethered template regions ("entangled mates") are returned simultaneously as a mixture of multiple signals from each template region. The mixed (i.e., entangled mate) sequencing signal is then disentangled into its constituent individual template sequences by matching the entangled sequence signature to its closest match in a reference collection of possibly occurring sequence signatures. This collection can be created using sequences obtained from one or more reference samples related to the sequence being analyzed, or more directly, from sequences representing the original template library.

In certain exemplary embodiments, methods of simultaneously determining nucleotide sequence identities of heterogeneous, tethered nucleic acid template sequences are provided. The methods include the steps of providing a mosaic target nucleic acid sequence including a first nucleic acid sequence and a second nucleic acid sequence, wherein the first and second nucleic acid sequences are tethered, determining a mixed nucleic acid sequence signature comprising the tethered first and second nucleic acid sequences, and comparing the nucleic acid sequence signature to a reference collection of sequence signatures to determine the nucleotide sequence identity of each of the tethered first and second nucleic acid sequences. In certain aspects, the heterogeneous, tethered nucleic acid sequences represent one or more of a genome, a proteome, a transcriptome or a cellular pathway. In other aspects, the heterogeneous, tethered nucleic acid sequences represent sequences derived from *Homo sapiens*.

In certain exemplary embodiments, methods of determining sequence identities of two tethered, heterogeneous nucleic acid sequences are provided. The methods include the steps of providing a heterogeneous library of mosaic target nucleic acids, in which a plurality include a first nucleic acid sequence and a second nucleic acid sequence, wherein the first and second nucleic acid sequences are tethered, determining a heterogeneous collection of mixed nucleic acid sequence signatures, each corresponding to a tethered pair of first and second nucleic acid sequences, and comparing the nucleic acid sequence signature to a reference collection of sequence signatures to determine the nucleotide sequence identity of each of the tethered first and second nucleic acid sequences. In certain aspects, the first nucleic acid sequences is a barcode sequence and the second nucleic acid sequence is a genomic sequence. In other aspects, the reference collection of sequence signatures is contained in a database. In still other aspects, the mosaic target nucleic acid sequence includes a first nucleic acid sequence, a second nucleic acid sequence and a third nucleic acid sequence, wherein the first, second and third nucleic acid sequences are tethered, and wherein the identity of each set of three bases extended from the 3' end of the first, second and third primers to determine a nucleic acid signature of the tightly co-localized linked first, second and third nucleic acid sequences is determined. In other aspects, the mosaic target nucleic acid sequence includes 3 or more tethered, nucleic acid sequences. In still other aspects, the mosaic target nucleic acid sequence is present on an array.

In certain exemplary embodiments, methods of simultaneously determining nucleotide sequence identities of two tethered nucleic acid sequences are provided. The methods include the steps of providing a heterogeneous library of mosaic target nucleic acids, in which a plurality include a first nucleic acid sequence and a second nucleic acid sequence, wherein the first and second nucleic acid sequences are tethered, annealing a first primer sequence to a portion of the first nucleic acid sequence and a second primer sequence to a portion of the second nucleic acid sequence, extending the annealed primers simultaneously, sequentially determining the identity of each set of two bases extended from the 3' ends of the first and second primers to determine a nucleic acid sequence signature of the tethered first and second nucleic acid sequences, and comparing the nucleic acid signature of the first nucleic acid sequence to a reference collection of sequence signatures to determine the nucleotide sequence identity of each of the tethered first and second nucleic acid sequences.

In certain aspects, the second nucleic acid sequence is not present in the reference collection of sequence signatures. In other aspects, each set of two bases is selected from the group consisting of AA, CC, GG, TT, AC, AG, AT, CG, CT and GT. In still other aspects, the first and second nucleic acid sequences are barcode sequences. In yet other aspects, the first and second nucleic acid sequences are genomic sequences. In other aspects, the first and second primer sequences have the same sequence identity or have a different sequence identity.

In certain exemplary embodiments, methods of identifying a cell type having heterogeneous nucleic acid sequences are provided. The methods include the steps of providing a cell having a mosaic target nucleic acid sequence including a first barcode sequence and a second barcode sequence, wherein the first and second barcode sequences are tethered, annealing a first primer sequence to a portion of the first barcode and a second primer sequence to a portion of the second barcode, extending the annealed primers simultaneously, determining a nucleic acid sequence signature of the first and second barcodes, and comparing the nucleic acid sequence signature to a reference collection of barcode sequence signatures to determine the identity of the cell. In certain aspects, the cell is a yeast cell. In other aspects, the yeast cell contains two or more alterations. In certain aspects, the heterogeneous nucleic acid sequences represent one or more of a genome, a proteome, a transcriptome or a cellular pathway. In still other aspects, the heterogeneous nucleic acid sequences represent Homo sapiens nucleic acid sequences.

Further features and advantages of certain embodiments of the present invention will become more fully apparent in the following description of the embodiments and drawings thereof, and from the claims.

BRIEF DESCRIPTION OF THE DRAWINGS

The foregoing and other features and advantages of the present invention will be more fully understood from the following detailed description of illustrative embodiments taken in conjunction with the accompanying drawings in which.

DETAILED DESCRIPTION

Figure 1:
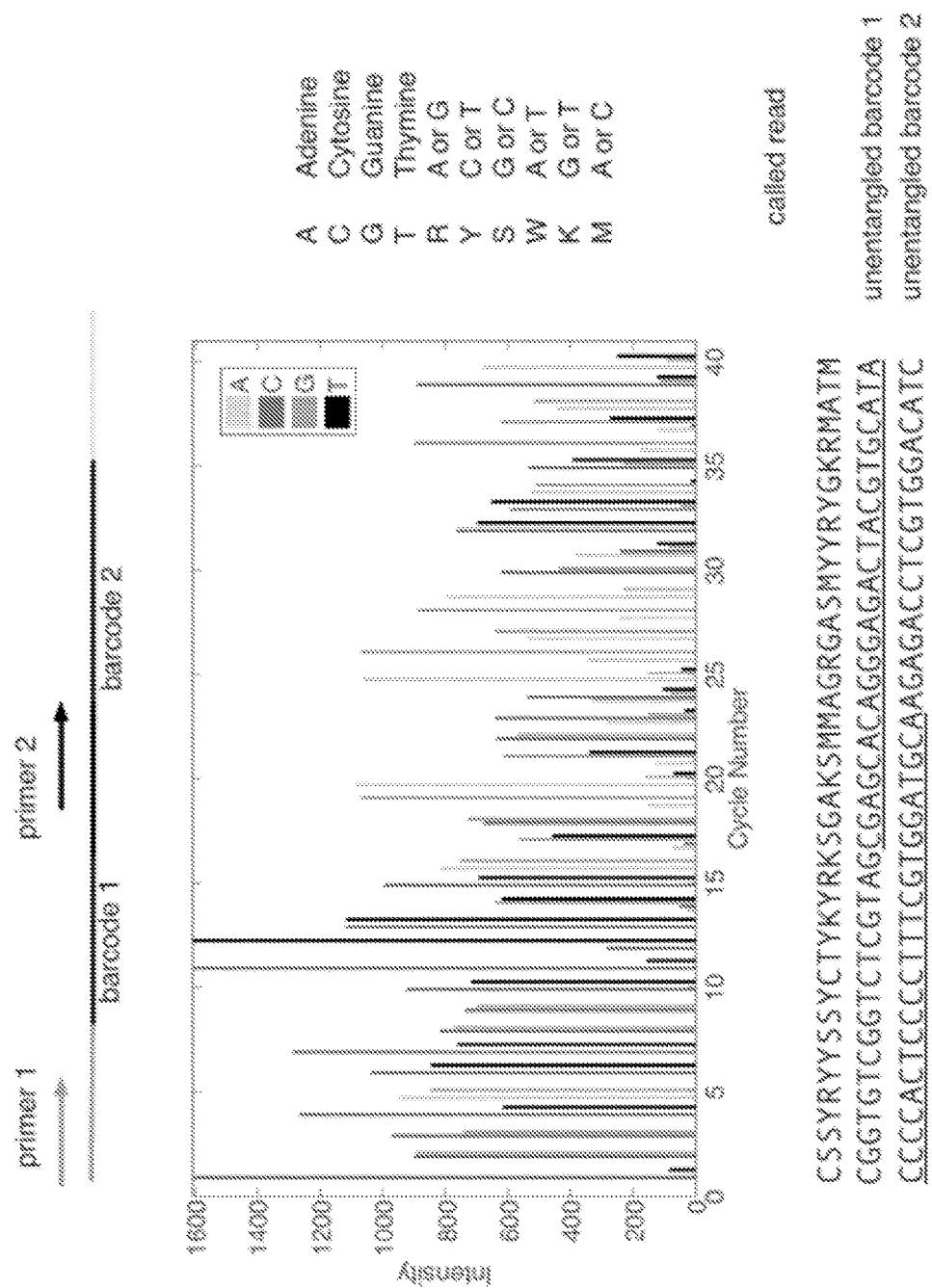
FIG. 1 depicts doubly-primed sequencing data from a single cluster on an Illumina GA2 flow cell, where the fragment was derived from a doubly-barcoded library. Each fragment in the library had two 24 base pair barcodes, flanked at the 3' end by universal priming sequences. Illumina GA2 sequencing was performed with a mix of the two universal primers (1 and 2). Using an adaptive threshold scheme, the intensity pattern at each cycle was then converted to the expanded nucleotide code shown at right (set forth as SEQ ID NO:1), which assigned a symbol to degenerate mixtures of two nucleotides. The "called read" was then compared to a reference database of sequence signatures corresponding to all possible pairs of single barcode sequences that were in the original library. Note that because the two primers had different offsets from the beginning of their flanking barcodes, only part of the read (underlined) corresponded to the two barcode sequences.

In certain exemplary embodiments, a method is provided for performing N DNA sequencing reaction cycles whereby at least 2*N nucleotide bases in a template nucleic acid sequence are queried simultaneously. In certain embodiments, the method includes the steps of: 1) preparing a library (e.g., a DNA library) for use in synchronously primed sequencing reactions; 2) sequencing two or more tethered nucleic acid sequences (e.g., present on one or more target sequences) with two or more sequencing probes; and 3) interpreting the sequencing data signals obtained from the two or more synchronously primed sequencing reactions. The methods and compositions described herein enable highly efficient sequencing from two (or more) tethered nucleic acid sequences, and can be used to determine the nucleic acid sequence of any source of target sequences.

In certain aspects, methods of re-sequencing a target genetic sequence (e.g., a genome) which has sequence homology to a known reference (e.g., genomic) sequence are provided. In certain aspects, such methods include the following steps: 1) producing a library (e.g., shotgun-cloned) of genomic DNA fragments; 2) constructing a database of entangled sequence signatures from all pairs of 'words' in a template genome that lie within a specified distance from one another, wherein that distance corresponds to the expected range of fragment sizes in the clone library; 3) producing an entangled sequence signature from tethered nucleic acid sequence reads (e.g., entangled reads) obtained from either end of a clone; and 4) scanning the database with the entangled sequence signature to identify close matches where a confident match that nonetheless exhibited difference from the expected entangled sequence signature would provide evidence for polymorphism.

In certain aspects, methods for mapping an entangled read to a reference genome are provided. For example, if only one component sequence of the entangled read matches the reference genome (exactly or approximately) and the other component contains sequence novel to the reference genome, it would be possible to identify a unique position in the reference genome that is consistent with the entangled read, such that the novel component of the entangled read may then be disentangled. Thus, information about novel sequences not found in a reference genome could be determined and constrained in their location relative to loci that match the template genome. For example, two common sequencing primers can be attached with inward orientation (via ligation or PCR) to the ends of a set of cloned genomic DNA fragments for sequencing. The genomic fragments could be purified to have relatively homogeneous length of L+/−Δ. During sequencing, the entangled sequence signal described above will be produced as a result of reading each consecutive nucleotide from both ends simultaneously. This entangled signal can then be matched to a reference genome sequence using the constraint that the mate sequences be of equal length and reverse complementary orientation with 5' ends separated by length L (+/−Δ).

In certain aspects, entangled mate sequencing is used to sequence a library of clone fragments wherein each library sequence carries a pair of DNA barcodes such that the pair in combination corresponds to a particular pair of alterations in the cell(s) from which the library sequence was derived. Each barcode sequence is flanked by a common pair of priming sites. For example, a given pair of barcode sequences can uniquely identify a cell (e.g., a yeast cell) harboring a specific pair of deletions, thus allowing complex populations of cells (e.g., yeast cells) with potentially thousands of different deletion pairs to be efficiently quantified. Quantifying the relative abundance of double-deletion strains before and after a selection is applied to the cells could identify particular pairs of genes that function adaptively in parallel, in concert or in series.

In other aspects, a given pair of barcode sequences can identify a cell (e.g., a yeast cell) harboring a specific pair of endogenous or heterologous (e.g., human) proteins respectively fused to DNA-binding and activation domains of a given transcription factor according to a two-hybrid system (e.g., a yeast two-hybrid system). This would allow complex populations of cells (e.g., yeast cells) carrying potentially thousands of different expressed heterologous protein pairs to be efficiently quantified. Quantifying the relative abundance of many strains within a population both before and after selection for expression of a reporter gene detecting interaction between the heterologous proteins could identify particular pairs of genes that respectively encode interacting heterologous proteins.

In certain aspects, methods and compositions for determining sequence information from two or more tethered nucleic acid sequences are provided. As used herein, the term "tethered nucleic acid sequences" refers to two or more nucleic acid sequences that are 1) physically linked to one another; or 2) are in close proximity to one another. In certain aspects, tethered nucleic acid sequences can be amplified to produce entangled nucleic acid sequences that contain two or more target nucleic acid sequences on the same nucleic acid molecule.

In certain exemplary embodiments, tethered nucleic acid sequences comprise a mosaic. As used herein, a "mosaic" refers to two or more different nucleic acid sequences (e.g., two or more multiply primed template sequences) that are tethered. In certain aspects, at least one sequence of the mosaic is a known sequence (e.g., a runway sequence). In other aspects, neither sequence of the mosaic is a known sequence.

Us used herein, the term "physical linkages" includes, but is not limited to, covalent interactions and noncovalent interactions. A covalent interaction is a chemical linkage between two atoms or radicals formed by the sharing of a pair of electrons (i.e., a single bond), two pairs of electrons (i.e., a double bond) or three pairs of electrons (i.e., a triple bond). Covalent interactions are also known in the art as electron pair interactions or electron pair bonds. Noncovalent interactions include, but are not limited to, van der Waals interactions, hydrogen bonds, weak chemical bonds (i.e., via short-range noncovalent forces), hydrophobic interactions, ionic bonds and the like. A review of noncovalent interactions can be found in Alberts et al., in *Molecular Biology of the Cell*, 3d edition, Garland Publishing, 1994. In certain aspects, tethered nucleic acids sequences that are physically linked to one another are located on the same nucleic acid molecule, e.g., via a covalent linkage (e.g., a phosphodiester linkage), a receptor-ligand interaction, a hapten-capture agent interaction (e.g., biotin-avidin) or the like. In certain aspects, nucleic acid sequences having a physical linkage have a linear distance from one another of less than 50 microns, 49 microns, 48 microns, 47 microns, 46 microns, 45 microns, 44 microns, 43 microns, 42 microns, 41 microns, 40 microns, 39 microns, 38 microns, 37 microns, 36 microns, 35 microns, 34 microns, 33 microns, 32 microns, 31 microns, 30 microns, 29 microns, 28 microns, 27 microns, 26 microns, 25 microns, 24 microns, 23 microns, 22 microns, 21 microns, 20 microns, 19 microns, 18 microns, 17 microns, 16 microns, 15 microns, 14 microns, 13 microns, 12 microns, 11 microns, 10 microns, 9 microns, 8 microns, 7 microns, 6 microns, 5 microns, 4 microns, 3 microns, 2 microns, 1 micron or less.

As used herein, the term "close proximity" refers to nucleic acid sequences that are close enough together that they are optically indistinguishable from one another (e.g., molecularly apposed), e.g., when they are indistinguishable from one another by microscopy (e.g., closer than would be expected on average if they were simply mixed in the same bulk solution). Examples of nucleic acid sequences that are in close proximity include, but are not limited to, sequences that are present within the same cell or cellular region, present on the same substrate (e.g., on the same array (e.g., a matrix), bead, DNA colony, RNA colony, PCR colony, emulsion droplet, nano bowl or the like) or present on two or more substrates that are brought together in close proximity (e.g., adjacent on an array, on two adjacent beads DNA colonies, RNA colonies, PCR colonies, nanoballs or the like or in two emulsion droplets that are mixed together, etc.). In certain aspects, nucleic acid sequences are in close proximity to one another when they are within 28 microns of one another. This spacing or closer spacing permits, for example, production of an emulsion of aqueous droplets (Tawfik, D. S. & Griffiths, A. D. (1998) *Nature Biotechnology* 16:652-656) such that some contain 28 micron beads (Shendure and Li (2008) *Nature Biotechnology* 26:1135-1145), and such that each bead-containing aqueous emulsion droplet will in general contain no nucleic acids, and such that a bead-containing aqueous droplet containing at least one nucleic acid will in general contain exactly one closely-proximal pair of nucleic acids. In certain aspects, nucleic acid sequences are in close proximity to one another when they are within 2 microns of one another. This spacing or closer spacing permits, for example, the placement of many clonal 'polymerase colonies' on a solid surface that are in general optically separated from one another (Bentley et al (2008) *Nature* 456:53-59), such that each colony would in general be seeded by a single closely-proximal pair of nucleic acid sequences. In certain aspects, nucleic acid sequences are in close proximity to one another when they are within 0.5 microns of one another. This spacing or closer spacing permits, for example, the placement of nucleic acids at generally optically separated locations for single-molecule sequencing (Harris et al. (2008) *Science* 320: 106-109) such that at any given nucleic acid sequencing template region on the surface would generally be optically indistinguishable with exactly one other nucleic acid sequencing template region. In other aspects, nucleic acid sequences are in close proximity to each other when they are within 50 microns, 49 microns, 48 microns, 47 microns, 46 microns, 45 microns, 44 microns, 43 microns, 42 microns, 41 microns, 40 microns, 39 microns, 38 microns, 37 microns, 36 microns, 35 microns, 34 microns, 33 microns, 32 microns, 31 microns, 30 microns, 29 microns, 28 microns, 27 microns, 26 microns, 25 microns, 24 microns, 23 microns, 22 microns, 21 microns, 20 microns, 19 microns, 18 microns, 17 microns, 16 microns, 15 microns, 14 microns, 13 microns, 12 microns, 11 microns, 10 microns, 9 microns, 8 microns, 7 microns, 6 microns, 5 microns, 4 microns, 3 microns, 2 microns, or 1 micron from one another.

As used herein, the term "entangled mate sequencing" refers to a method of determining the nucleic acid sequence of two or more tethered nucleic acid sequences (e.g., entangled nucleic acid sequences). When the nucleotide sequence of a single deoxyribonucleic acid sequence is determined, four possible results are typically expected at each read position: G, A, T (U for ribonucleic acid) or C. When the nucleotide sequence of two tethered deoxyribonucleic acid sequences (e.g., entangled mates) are queried simultaneously, ten possible results are expected at each read position (one base from each of the two deoxyribonucleic acid sequences): AA, CC, GG, TT (UU for ribonucleic acid), AC, AG, AT (AU for ribonucleic acid), CG, CT (CU for ribonucleic acid) or GT (GU for ribonucleic acid). Each of these ten pairs of bases has a unique signature that can be identified (e.g., by eye from an autoradiograph, by fluorescence detection or the like).

When the nucleotide sequence of three tethered deoxyribonucleic acid sequences (e.g., entangled trios) are queried simultaneously, 20 possible results are expected at each read position (one base from each of the three deoxyribonucleic acid sequences): AAA, AAC, AAG, AAT (AAU for ribonucleic acid), ACC, ACG, ACT (ACU for ribonucleic acid), AGG, AGT (AGU for ribonucleic acid), ATT (AUU for ribonucleic acid), CCC, CCG, CCT (CCU for ribonucleic acid), CGG, CGT (CGU for ribonucleic acid), CTT (CUU for ribonucleic acid), GGG, GGT (GGU for ribonucleic acid), GTT (GUU for ribonucleic acid), TTT (UUU for ribonucleic acid). Each of these 20 trios of bases has a unique signature that can be identified (e.g., by eye from an autoradiograph, by fluorescence detection or the like).

In certain exemplary embodiments, a plurality of entangled nucleic acid sequences are provided. In certain aspects, at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86% 87, 88%, 89%, 90%, 91%, 92%, 93%, 94%, 95%, 96%, 97%, 98%, 99.0%, 99.1%, 99.2%, 99.3%, 99.4%, 99.5%, 99.6%, 99.7%, 99.8%, 99.9% or more of the nucleic acid sequences provided (e.g., in a sample or on a substrate) are entangled.

The signal obtained from a conventional cycle of nucleotide sequencing is typically in the form of detection of one or more fluorescent or chemiluminescent labels corresponding to the presence a corresponding one or more unique nucleotide(s) at a unique position in the template molecule sequence. In entangled mate sequencing, each such chemistry cycle produces a detectable signal corresponding to the presence of at least two nucleotide(s) that are at different positions of the template molecule, or on different template molecules that are otherwise tethered. Just as conventional nucleotide sequencing depends on nucleotide "base calling" methods for determining the identity of the nucleotide(s) at a single location in a template molecule, entangled base calling depends on the ability to infer the nucleotide(s) from multiple locations in a template.

Entangled mate sequencing uses either of two methods for entangled base calling: "purity-based" or "cluster-based." In "purity-based" base calling, the nucleotide(s) signals with the highest nominal signal intensity are measured for purity or signal relative to that of less-intense nucleotides in the same chemistry cycle. If R is the intensity ratio of the Nth most intense base to the next-most-intense base at a given position, then some a priori threshold R* is used to determine if the "correct" call at cycle one includes either the top N=1 or N=2 nucleotides based on the available intensity signals. In practice, values of R*=1.6 can effectively distinguish the correct call at a given position. In "cluster-based" base calling, the raw intensities of many different reads at the same cycle are first classified into separable clusters using algorithmic clustering (e.g., by Gaussian mixture-modeling). Using this approach, each single entangled read is then assigned to one of the learned clusters that represents the consensus intensity signal of a given unique entangled base-call.

Methods for determining the nucleic acid sequence of two or more tethered nucleic acid sequences can be performed using a variety of sequencing methods known in the art including, but not limited to, Maxam-Gilbert sequencing, chain termination sequencing (e.g., Sanger dideoxy sequencing), dye-terminator sequencing, sequencing by hybridization (SBH), sequencing by ligation (SBL), quantitative incremental fluorescent nucleotide addition sequencing (QIFNAS), stepwise ligation and cleavage, fluorescence resonance energy transfer (FRET), molecular beacons, TaqMan reporter probe digestion, pyrosequencing, fluorescent in situ sequencing (FISSEQ), FISSEQ beads (U.S. Pat. No. 7,425,431), wobble sequencing (PCT/US05/27695), multiplex sequencing (U.S. Ser. No. 12/027,039, filed Feb. 6, 2008; Porreca et al (2007) *Nat. Methods* 4:931), polymerized colony (POLONY) sequencing (U.S. Pat. Nos. 6,432,360, 6,485,944 and 6,511,803, and PCT/US05/06425); nanogrid rolling circle sequencing (ROLONY) (U.S. Ser. No. 12/120,541, filed May 14, 2008), allele-specific oligo ligation assays (e.g., oligo ligation assay (OLA), single template molecule OLA using a ligated linear probe and a rolling circle amplification (RCA) readout, ligated padlock probes, and/or single template molecule OLA using a ligated circular padlock probe and a rolling circle amplification (RCA) readout) and the like. High-throughput sequencing methods, e.g., on cyclic array sequencing using platforms such as Illumina flow cell, ABI, Complete Genomics' Nano Bowl, Roche 454, Illumina Solexa, AB-SOLiD, Helicos, Polonator platforms and the like, can also be utilized. High-throughput sequencing methods are described in U.S. Ser. No. 61/162,913, filed Mar. 24, 2009. A variety of light-based sequencing technologies are known in the art (Landegren et al. (1998) *Genome Res.* 8:769-76; Kwok (2000) *Pharmocogenomics* 1:95-100; and Shi (2001) *Clin. Chem.* 47:164-172).

In certain aspects, one or more reference collections of signatures are provided for comparison with the nucleic acid sequence of two or more tethered nucleic acid sequences (i.e., a query nucleic acid sequence signature). As used herein, a "database of reference sequence signatures" includes, but is not limited to, the nucleic acid sequence signature corresponding to a first nucleic acid sequence tethered to a second nucleic acid sequence and comprises a plurality of unique sequence signatures corresponding to all possible pairs that could be obtained at each sequencing position for the first and second nucleic acid sequences. In certain aspects, a reference collection of sequence signatures includes sequence data corresponding to a plurality of heterogeneous reference sequences. In certain aspects, a reference collection of sequence signatures could comprise a barcode library, a genomic library, an exon library, an intron library, an intergenic DNA library (including, without limitation, a heterochromatic DNA library), a messenger RNA (mRNA) library, a transfer RNA library, a ribosomal RNA library, a ribozyme library, a small interfering RNA (siRNA) library, cDNA library or the like.

In certain aspects, a query nucleic acid sequence signature will have 100% sequence identity to a reference collection nucleic acid sequence signature. In other aspects, a query nucleic acid sequence signature will have about 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71% or 70% sequence identity to a reference collection nucleic acid sequence signature. In yet other aspects, a query nucleic acid sequence signature will have between about 100% and 70%, between about 100% and 80%, between about 100% and 90% or between about 100% and 95% sequence identity to a reference collection nucleic acid sequence signature. In still other aspects, a query nucleic acid sequence signature will have greater than about 70%, 80%, 90% or 95% sequence identity to a reference collection nucleic acid sequence signature.

In certain aspects, the query nucleic acid sequences will be represented as "entangled matrices," which are 4×L matrices such that 4 is the number of bases and L is the length of the query entangled sequence, with each entry in the matrix being a quantitative value that correlates with the presence of a given nucleotide at a given position in the entangled sequence. In certain aspects, reference collection nucleic acid sequences will be represented as entangled matrices. In certain aspects, similarity between query and reference collection nucleic acid sequences will be measured by comparing a query entangled matrix with a reference collection entangled matrix, by comparing a query entangled matrix with a reference collection nucleic acid sequence, or by comparing a query entangled sequence with a reference collection entangled matrix.

In certain exemplary embodiments, computer software is provided to automate design and/or analysis of query nucleic acid sequence signatures and/or reference collection nucleic acid sequence signatures. In at least some embodiments, the gene/oligonucleotide design software is implemented in a program written in the JAVA programming language. The program may be compiled into an executable that may then be run from a command prompt in the WINDOWS XP operating system. Unless specifically set forth in the claims, however, the invention is not limited to implementation using a specific programming language, operating system environment or hardware platform.

In certain exemplary embodiments, methods and compositions for using molecular barcodes to identify various combinations of mutations or deletions within a cell are provided. As used herein, the term "barcode" refers to a unique DNA sequence that can be used to flank one or both ends of each deletion or genetic alteration, in an organism, e.g., yeast. The terms "barcoded mutation" and "barcode-associated mutation" as used herein, refer to a deletion or genetic alteration flanked on one or both ends by a barcode.

The term "stitched barcode" may refer to many DNA sequences, or many barcodes, representing many genetic alterations, for example, when numerous barcodes are linked together. Barcode assays are particularly useful for determining the genetic basis of drug sensitivity and resistance. Barcode technologies are known in the art (see Winzeler et al. (1999) *Science* 285:901; Brenner (2000) *Genome Biol.* 1:1; Kumar et al. (2001) *Nature Rev.* 2:302; Giaever et al. (2004) *Proc. Natl. Acad. Sci.* USA 101:793; Eason et al. (2004) *Proc. Natl. Acad. Sci.* USA 101:11046; and Brenner (2004) *Genome Biol.* 5:240).

The use of barcodes for screening fitness in mutants is not limited to strains or organisms having engineered barcodes marking null (e.g., deletion) or other mutant alleles only. Unique DNA barcodes can be incorporated by those skilled in the art into genetic vectors of various origin for the purpose of identifying the presence of a vector in a pool of engineered strains. Similarly, pairs of barcodes can be used in pools of strains to identify which strains carry a given pair of engineered genetic vectors. Engineered, genetic vectors are routinely used to screen for interactions in complementation assays such as yeast two hybrid to identify pairs of protein fragments that interact (See Walhout et al. High-throughput yeast two hybrid assays for large-scale protein interaction mapping. *Methods* (2001) 24(3):297-306). Measurements of relative abundance (thereby measuring relative growth rates) for strains carrying other combinations of alterations can also be informative. For example, the combination of a mutant allele at one locus with an engineered gene expressed at high levels at a second locus can be used, for example, to understand kinase-substrate relationships (See, for example, Sopko et al. (2008) *Mol. Biosyst.* 4:920) and literature on synthetic dosage lethality interactions discussed therein).

In certain aspects, methods of "stitching" one or more DNA barcodes or other nucleic acid sequences together in a single reaction which allows the stitched barcode to be identified by one sequencing reaction are provided. As used herein, the term "stitching" refers to the linking of a plurality of molecular barcodes and/or nucleic acid sequences, for example, via an amplification reaction such as barcode crossover PCR, or an extension reaction.

In certain aspects, methods of amplifying nucleic acid sequences (e.g., entangled mates, target nucleic acid sequences, one or both of two tethered nucleic acid sequences and the like) are provided. Exemplary methods for amplifying nucleic acids include the polymerase chain reaction (PCR) (see, e.g., Mullis et al. (1986) *Cold Spring Harb. Symp. Quant. Biol.* 51 Pt 1:263 and Cleary et al. (2004) *Nature Methods* 1:241; and U.S. Pat. Nos. 4,683,195 and 4,683,202), anchor PCR, RACE PCR, ligation chain reaction (LCR) (see, e.g., Landegran et al. (1988) *Science* 241:1077-1080; and Nakazawa et al. (1994) *Proc. Natl. Acad. Sci. U.S.A.* 91:360-364), self sustained sequence replication (Guatelli et al. (1990) *Proc. Natl. Acad. Sci. U.S.A.* 87:1874), transcriptional amplification system (Kwoh et al. (1989) *Proc. Natl. Acad. Sci. U.S.A.* 86:1173), Q-Beta Replicase (Lizardi et al. (1988) *BioTechnology* 6:1197), recursive PCR (Jaffe et al. (2000) *J. Biol. Chem.* 275:2619; and Williams et al. (2002) *J. Biol. Chem.* 277: 7790), the amplification methods described in U.S. Pat. Nos. 6,391,544, 6,365,375, 6,294,323, 6,261,797, 6,124,090 and 5,612,199, isothermal amplification (e.g., rolling circle amplification (RCA), hyperbranched rolling circle amplification (HRCA), strand displacement amplification (SDA), helicase-dependent amplification (HDA), PWGA) or any other nucleic acid amplification method using techniques well known to those of skill in the art, polymerase and/or ligase chain reactions, thermal cycling (PCR) or isothermally (e.g. RCA, hRCA, SDA, HDA, PWGA (Worldwide Website: biohelix.com/technology.asp)).

In certain aspects, at least one of the tethered nucleic acid sequences is comprised of a fixed or known nucleic acid sequence identity, termed here as a 'runway' sequence. Among other uses, the runway sequence can be used to obtain an unambiguous nucleotide sequence for part of the unknown portion of the tethered sequences. In some cases, the sequence of the unknown portion derived from un-entangling the runway portion can assist the process of assigning a match of the unknown portion to the reference collection of nucleic acid sequences database. In certain aspects, a runway sequence can be used to obtain reads that are at least 50 bp, 60 bp, 70 bp, 80 bp, 90 bp, 100 bp, 110 bp, 120 bp, 130 bp, 140 bp, 150 bp, 160 bp, 170 bp, 180 bp, 190 bp, 200 bp or more by in length.

PCR refers to a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g., exemplified by the references: McPherson et al., editors, *PCR: A Practical Approach and PCR2: A Practical Approach* (IRL Press, Oxford, 1991 and 1995, respectively). For example, in a conventional PCR using Taq DNA polymerase, a double stranded target nucleic acid may be denatured at a temperature greater than 90° C., primers annealed at a temperature in the range 50-75° C., and primers extended at a temperature in the range 72-78° C.

The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g., 200 mL, to a few hundred microliters, e.g., 200 microliters. "Reverse transcription PCR," or "RT-PCR," means a PCR that is preceded by a reverse transcription reaction that converts a target RNA to a complementary single stranded DNA, which is then amplified, e.g., Tecott et al., U.S. Pat. No. 5,168,038. "Real-time PCR" means a PCR for which the amount of reaction product, i.e., amplicon, is monitored as the reaction proceeds. There are many forms of real-time PCR that differ mainly in the detection chemistries used for monitoring the reaction product, e.g., Gelfand et al., U.S. Pat. No. 5,210,015 ("Taqman"); Wittwer et al., U.S. Pat. Nos. 6,174,670 and 6,569,627 (intercalating dyes); Tyagi et al., U.S. Pat. No. 5,925,517 (molecular beacons). Detection chemistries for real-time PCR are reviewed in Mackay et al., *Nucleic Acids Research,* 30:1292-1305 (2002). "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al. (1999) *Anal. Biochem.*, 273:221-228 (two-color real-time PCR). Usually, distinct sets of primers are employed for each sequence being amplified. "Quantitative PCR" means a PCR designed to measure the abundance of one or more specific target sequences in a sample or specimen. Quantitative PCR includes both absolute quantitation and relative quantitation of such target sequences. Techniques for quantitative PCR are well-known to those of ordinary skill in the art, as exemplified in the following references: Freeman et al., *Biotechniques*, 26:112-126 (1999); Becker-Andre et al., *Nucleic Acids Research*, 17:9437-9447 (1989); Zimmerman et al., *Biotechniques*, 21:268-279 (1996); Diviacco et al., *Gene*, 122:3013-3020 (1992); Becker-Andre et al., *Nucleic Acids Research*, 17:9437-9446 (1989); and the like.

Terms and symbols of nucleic acid chemistry, biochemistry, genetics, and molecular biology used herein follow those of standard treatises and texts in the field, e.g., Komberg and Baker, *DNA Replication*, Second Edition (W.H. Freeman, New York, 1992); Lehninger, *Biochemistry*, Second Edition (Worth Publishers, New York, 1975); Strachan and Read, *Human Molecular Genetics*, Second Edition (Wiley-Liss, New York, 1999); Eckstein, editor, *Oligonucleotides and Analogs: A Practical Approach* (Oxford University Press, New York, 1991); Gait, editor, *Oligonucleotide Synthesis: A Practical Approach* (IRL Press, Oxford, 1984); and the like.

"Complementary" or "substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid. Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See Kanehisa (1984) *Nucl. Acids Res.* 12:203. According to the present invention, useful MIP primer sequences hybridize to sequences that flank the nucleotide base or series of bases to be captured.

"Complex" means an assemblage or aggregate of molecules in direct or indirect contact with one another. In one aspect, "contact," or more particularly, "direct contact," in reference to a complex of molecules or in reference to specificity or specific binding, means two or more molecules are close enough so that attractive noncovalent interactions, such as van der Waal forces, hydrogen bonding, ionic and hydrophobic interactions, and the like, dominate the interaction of the molecules. In such an aspect, a complex of molecules is stable in that under assay conditions the complex is thermodynamically more favorable than a non-aggregated, or non-complexed, state of its component molecules. As used herein, "complex" refers to a duplex or triplex of polynucleotides or a stable aggregate of two or more proteins. In regard to the latter, a complex is formed by an antibody specifically binding to its corresponding antigen.

"Duplex" means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. In one aspect, stable duplex means that a duplex structure is not destroyed by a stringent wash, e.g., conditions including temperature of about 5° C. less that the $T_m$ of a strand of the duplex and low monovalent salt concentration, e.g., less than 0.2 M, or less than 0.1 M. "Perfectly matched" in reference to a duplex means that the polynucleotide or oligonucleotide strands making up the duplex form a double stranded structure with one another such that every nucleotide in each strand undergoes Watson-Crick base pairing with a nucleotide in the other strand. The term "duplex" comprehends the pairing of nucleoside analogs, such as deoxyinosine, nucleosides with 2-aminopurine bases, PNAs, and the like, that may be employed. A "mismatch" in a duplex between two oligonucleotides or polynucleotides means that a pair of nucleotides in the duplex fails to undergo Watson-Crick bonding.

"Genetic locus," or "locus" in reference to a genome or target polynucleotide, means a contiguous subregion or segment of the genome or target polynucleotide. As used herein, genetic locus, or locus, may refer to the position of a nucleotide, a gene, or a portion of a gene in a genome, including mitochondrial DNA, or it may refer to any contiguous portion of genomic sequence whether or not it is within, or associated with, a gene. In one aspect, a genetic locus refers to any portion of genomic sequence, including mitochondrial DNA, from a single nucleotide to a segment of few hundred nucleotides, e.g. 100-300, in length. Usually, a particular genetic locus may be identified by its nucleotide sequence, or the nucleotide sequence, or sequences, of one or both adjacent or flanking regions. In another aspect, a genetic locus refers to the expressed nucleic acid product of a gene, such as an RNA molecule or a cDNA copy thereof.

"Hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex." "Hybridization conditions" will typically include salt concentrations of less than about 1 M, more usually less than about 500 mM and even more usually less than about 200 mM. Hybridization temperatures can be as low as 5° C., but are typically greater than 22° C., more typically greater than about 30° C., and often in excess of about 37° C. Hybridizations are usually performed under stringent conditions, i.e., conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the $T_m$ for the specific sequence at s defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM Na phosphate, 5 mM EDTA, pH 7.4) and a temperature of 25-30° C. are suitable for allele-specific probe hybridizations. For stringent conditions, see for example, Sambrook, Fritsche and Maniatis, *Molecular Cloning A Laboratory Manual*, 2nd Ed. Cold Spring Harbor Press (1989) and Anderson *Nucleic Acid Hybridization*, 1$^{st}$ Ed., BIOS Scientific Publishers Limited (1999). "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

"Hybridization-based assay" means any assay that relies on the formation of a stable complex as the result of a specific binding event. In one aspect, a hybridization-based assay means any assay that relies on the formation of a stable duplex or triplex between a probe and a target nucleotide sequence for detecting or measuring such a sequence. In one aspect, probes of such assays anneal to (or form duplexes with) regions of target sequences in the range of from 8 to 100 nucleotides; or in other aspects, they anneal to target sequences in the range of from 8 to 40 nucleotides, or more usually, in the range of from 8 to 20 nucleotides. A "probe" in reference to a hybridization-based assay means a polynucleotide that has a sequence that is capable of forming a stable hybrid (or triplex) with its complement in a target nucleic acid and that is capable of being detected, either directly or indirectly. Hybridization-based assays include, without limitation, assays that use the specific base-pairing of one or more oligonucleotides as target recognition components, such as polymerase chain reactions, NASBA reactions, oligonucleotide ligation reactions, single-base extension reactions, circularizable probe reactions, allele-specific oligonucleotide hybridizations, either in solution phase or bound to solid phase supports, such as microarrays or microbeads, and the like. An important subset of hybridization-based assays include such assays that have at least one enzymatic processing step after a hybridization step. Hybridization-based assays of this subset include, without limitation, polymerase chain reactions, NASBA reactions, oligonucleotide ligation reactions, cleavage reactions, e.g., in INVADER™ assays, single-base extension reactions, probe circularization reactions, and the like. There is extensive guidance in the literature on hybridization-based assays, e.g., Hames et al., editors, *Nucleic Acid Hybridization a Practical Approach* (IRL Press, Oxford, 1985); Tijssen, *Hybridization with Nucleic Acid Probes*, Parts I & II (Elsevier Publishing Company, 1993); Hardiman, *Microarray Methods and Applications* (DNA Press, 2003); Schena, editor, *DNA Microarrays a Practical Approach* (IRL Press, Oxford, 1999); and the like. In one aspect, hybridization-based assays are solution phase assays; that is, both probes and target sequences hybridize under conditions that are substantially free of surface effects or influences on reaction rate. A solution phase assay includes circumstances where either probes or target sequences are attached to microbeads such that the attached sequences have substantially the same environment (e.g., permitting reagent access, etc.) as free sequences. In another aspect, hybridization-based assays include immunoassays wherein antibodies employ nucleic acid reporters based on amplification. In such assays, antibody probes specifically bind to target molecules, such as proteins, in separate reactions, after which the products of such reactions (i.e., antibody-protein complexes) are combined and nucleic acid reporters are amplified. Preferably, such nucleic acid reporters include oligonucleotide tags that are converted enzymatically into labeled oligonucleotide tags for analysis on a microarray, as described below. The following exemplary references disclose antibody-nucleic acid conjugates for immunoassays: Baez et al., U.S. Pat. No. 6,511,809; Sano et al., U.S. Pat. No. 5,665,539; Eberwine et al., U.S. Pat. No. 5,922,553; Landegren et al., U.S. Pat. No. 6,558,928; Landegren et al., U.S. Patent Pub. 2002/0064779; and the like. In particular, the two latter patent publications by Landegren et al. disclose steps of forming amplifiable probes after a specific binding event.

"Kit" refers to any delivery system for delivering materials or reagents for carrying out a method of the invention. In the context of assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials for assays of the invention. Such contents may be delivered to the intended recipient together or separately. For example, a first container may contain an enzyme for use in an assay, while a second container contains probes.

"Ligation" means to form a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references: Whitely et al., U.S. Pat. No. 4,883,750; Letsinger et al., U.S. Pat. No. 5,476,930; Fung et al., U.S. Pat. No. 5,593,826; Kool, U.S. Pat. No. 5,426,180; Landegren et al., U.S. Pat. No. 5,871,921; Xu and Kool (1999) *Nucl. Acids Res.* 27:875; Higgins et al., *Meth. in Enzymol.* (1979) 68:50; Engler et al. (1982) *The Enzymes,* 15:3 (1982); and Namsaraev, U.S. Patent Pub. 2004/0110213.

"Microarray" refers in one embodiment to a type of multiplex assay product that comprises a solid phase support having a substantially planar surface on which there is an array of spatially defined non-overlapping regions or sites that each contain an immobilized hybridization probe. "Substantially planar" means that features or objects of interest, such as probe sites, on a surface may occupy a volume that extends above or below a surface and whose dimensions are small relative to the dimensions of the surface. For example, beads disposed on the face of a fiber optic bundle create a substantially planar surface of probe sites, or oligonucleotides disposed or synthesized on a porous planar substrate creates a substantially planar surface. Spatially defined sites may additionally be "addressable" in that its location and the identity of the immobilized probe at that location are known or determinable. Probes immobilized on microarrays include nucleic acids, such as oligonucleotide barcodes, that are generated in or from an assay reaction. Typically, the oligonucleotides or polynucleotides on microarrays are single stranded and are covalently attached to the solid phase support, usually by a 5'-end or a 3'-end. The density of non-overlapping regions containing nucleic acids in a microarray is typically greater than 100 per cm$^2$, and more preferably, greater than 1000 per cm$^2$. Microarray technology relating to nucleic acid probes is reviewed in the following exemplary references: Schena, Editor, *Microarrays: A Practical Approach* (IRL Press, Oxford, 2000); Southern, *Current Opin. Chem. Biol.*, 2: 404-410 (1998); *Nature Genetics Supplement*, 21:1-60 (1999); and Fodor et al., U.S. Pat. Nos. 5,424,186; 5,445,934; and 5,744,305. A microarray may comprise arrays of microbeads, or other microparticles, alone or disposed on a planar surface or in wells or other physical configurations that can be sued to separate the beads. Such microarrays may be formed in a variety of ways, as disclosed in the following exemplary references: Brenner et al. (2000) *Nat. Biotechnol.* 18:630; Tulley et al., U.S. Pat. No. 6,133,043; Stuelpnagel et al., U.S. Pat. No. 6,396,995; Chee et al., U.S. Pat. No. 6,544,732; and the like. In one format, microarrays are formed by randomly disposing microbeads having attached oligonucleotides on a surface followed by determination of which microbead carries which oligonucleotide by a decoding procedure, e.g. as disclosed by Gunderson et al., U.S. Patent Pub. No. 2003/0096239.

"Microarrays" or "arrays" can also refer to a heterogeneous pool of nucleic acid molecules that is distributed over a support matrix. The nucleic acids can be covalently or noncovalently attached to the support. Preferably, the nucleic acid molecules are spaced at a distance from one another sufficient to permit the identification of discrete features of the array. Nucleic acids on the array may be non-overlapping or partially overlapping. Methods of transferring a nucleic acid pool to support media is described in U.S. Pat. No. 6,432,360. Bead based methods useful for the methods described herein are disclosed in PCT US05/04373.

"Amplifying" includes the production of copies of a nucleic acid molecule of the array or a nucleic acid molecule bound to a bead via repeated rounds of primed enzymatic synthesis. "In situ" amplification indicated that the amplification takes place with the template nucleic acid molecule positioned on a support or a bead, rather than in solution. In situ amplification methods are described in U.S. Pat. No. 6,432,360.

"Support" can refer to a matrix upon which nucleic acid molecules of a nucleic acid array are placed. The support can be solid or semi-solid or a gel. "Semi-solid" refers to a compressible matrix with both a solid and a liquid component, wherein the liquid occupies pores, spaces or other interstices between the solid matrix elements. Semi-solid supports can be selected from polyacrylamide, cellulose, polyamide (nylon) and crossed linked agarose, dextran and polyethylene glycol.

"Randomly-patterned" or "random" refers to non-ordered, non-Cartesian distribution (in other words, not arranged at pre-determined points along the x- or y-axes of a grid or at defined "clock positions," degrees or radii from the center of a radial pattern) of nucleic acid molecules over a support, that is not achieved through an intentional design (or program by which such design may be achieved) or by placement of individual nucleic acid features. Such a "randomly-patterned" or "random" array of nucleic acids may be achieved by dropping, spraying, plating or spreading a solution, emulsion, aerosol, vapor or dry preparation comprising a pool of nucleic acid molecules onto a support and allowing the nucleic acid molecules to settle onto the support without intervention in any manner to direct them to specific sites thereon. Arrays of the invention can be randomly patterned or random.

"Heterogeneous" refers to a population or collection of nucleic acid molecules that comprises a plurality of different sequences. According to one aspect, a heterogeneous pool of nucleic acid molecules results from a preparation of RNA or DNA from a cell which may be unfractionated or partially-fractionated. In certain aspects, a heterogeneous population of nucleic acid sequences includes one or more of a genome, a proteome (e.g., nucleic acid sequences encoding a proteome), a transcriptome, a cellular pathway, a collection of DNA or RNA from barcoded populations of cells, a reduced representation library, a library derived from targeted enrichment (e.g., an exome library), one or more sorted chromosomes, a mixtures of two or more different libraries (e.g., a cancer and matched normal sample combined) and the like.

As used herein, a "genome" refers to the entirety of an organism's hereditary information. It is encoded either in DNA or, as for many types of viruses, in RNA. The genome includes both genes and the non-coding sequences of the DNA.

As used herein, a "proteome" refers to the entire set of proteins expressed by a genome, cell, tissue or organism. In certain aspects, it is the set of expressed proteins in a given type of cell or organism at a given time under defined conditions. The term has been applied to several different types of biological systems. A cellular proteome refers to a collection of proteins found in a particular cell type under a particular set of environmental conditions (e.g., such as exposure to hormone stimulation). It can also be useful to consider an organism's complete proteome, which can be conceptualized as the complete set of proteins from all of the various cellular proteomes. This is very roughly the protein equivalent of the genome. The term proteome has also been used to refer to the collection of proteins in certain sub-cellular biological systems. For example, all of the proteins in a virus can be called a viral proteome.

As used herein, a "transcriptome" refers to the set of all RNA molecules, including mRNA, rRNA, tRNA, and non-coding RNA produced in one or a population of cells. The term can be applied to the total set of transcripts in a given organism, or to the specific subset of transcripts present in a particular cell type. The transcriptome can vary with external environmental conditions. Because it includes all mRNA transcripts in the cell, the transcriptome reflects the genes that are being actively expressed at any given time, with the exception of mRNA degradation phenomena such as transcriptional attenuation. The study of transcriptomics, also referred to as expression profiling, examines the expression level of mRNAs in a given cell population, often using high-throughput techniques based on DNA microarray technology. The use of next-generation sequencing technology to study the transcriptome at the nucleotide level is known as RNA-Seq (Wang et al. (2009) *Nature Rev. Genetics* 10:57).

As used herein, a "cellular pathway" refers to one or more series of events that may occur in one or more cells and/or organisms including, but not limited to, a metabolic pathway (e.g., nucleotide metabolism, carbohydrate metabolism, amino acid metabolism, lipid metabolism, co-factor metabolism, vitamin metabolism, energy metabolism and the like), a signaling pathway, a biosynthetic pathway, an immunological pathway, a developmental pathway and the like.

In certain aspects, a heterogeneous population of nucleic acid molecules comprises at least 100, 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 25,000, 30,000, 35,000, 40,000, 45,000, 50,000, 55,000, 60,000, 65,000, 70,000, 75,000, 80,000, 85,000, 90,000, 95,000, 100,000, 150,000, 200,000, 250, 000, 300,000, 350,000, 400,000, 450,000, 500,000, 550,000, 600,000, 650,000, 700,000, 750,000, 800,000, 8500,000, 900,000, 950,000, 1,000,000, 2,000,000, 3,000,000, 4,000, 000, 5,000,000, 6,000,000, 7,000,000, 8,000,000, 9,000,000, 10,000,000, 100,000,000, 1,000,000,000, or more distinct nucleic acid sequences. In other aspects, a heterogeneous population of nucleic acid molecules comprises at least 10 kb, 100 kb, 200 kb, 300 kb, 400 kb, 500 kb, 600 kb, 700 kb, 800 kb, 900 kb, 1 Mb, 2 Mb, 3 Mb, 4 Mb, 5 Mb, 6 Mb, 7 Mb, 8 Mb, 9 Mb, 10 Mb, 11 Mb, 12 Mb, 13 Mb, 14 Mb, 15 Mb, 16 Mb, 17 Mb, 18 Mb, 19 Mb, 20 Mb, 21 Mb, 22 Mb, 23 Mb, 24 Mb, 25 Mb, 26 Mb, 27 Mb, 28 Mb, 29 Mb, 30 Mb, 31 Mb, 32 Mb, 33 Mb, 34 Mb, 35 Mb, 36 Mb, 37 Mb, 38 Mb, 39 Mb, 40 Mb, 41 Mb, 42 Mb, 43 Mb, 44 Mb, 45 Mb, 46 Mb, 47 Mb, 48 Mb, 49 Mb, 50 Mb, 51 Mb, 52 Mb, 53 Mb, 54 Mb, 55 Mb, 56 Mb, 57 Mb, 58 Mb, 59 Mb, 60 Mb, 61 Mb, 62 Mb, 63 Mb, 64 Mb, 65 Mb, 66 Mb, 67 Mb, 68 Mb, 69 Mb, 70 Mb, 71 Mb, 72 Mb, 73 Mb, 74 Mb, 75 Mb, 76 Mb, 77 Mb, 78 Mb, 79 Mb, 80 Mb, 81 Mb, 82 Mb, 83 Mb, 84 Mb, 85 Mb, 86 Mb, 87 Mb, 88 Mb, 89 Mb, 90 Mb, 91 Mb, 92 Mb, 93 Mb, 94 Mb, 95 Mb, 96 Mb, 97 Mb, 98 Mb, 99 Mb, 100 Mb, or more of sequence.

"Nucleoside" as used herein includes the natural nucleosides, including 2'-deoxy and 2'-hydroxyl forms, e.g. as described in Komberg and Baker, *DNA Replication,* 2nd Ed. (Freeman, San Francisco, 1992). "Analogs" in reference to nucleosides includes synthetic nucleosides having modified base moieties and/or modified sugar moieties, e.g., described by Scheit, *Nucleotide Analogs* (John Wiley, New York, 1980); Uhlman and Peyman, *Chemical Reviews,* 90:543-584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above); Crooke et al., *Exp. Opin. Ther. Patents,* 6: 855-870 (1996); Mesmaeker et al., *Current Opinion in Structural Biology,* 5:343-355 (1995); and the like. Exemplary types of polynucleotides that are capable of enhancing duplex stability include oligonucleotide phosphoramidates (referred to herein as "amidates"), peptide nucleic acids (referred to herein as "PNAs"), oligo-2'-O-alkylribonucleotides, polynucleotides containing C-5 propynylpyrimidines, locked nucleic acids (LNAs), and like compounds. Such oligonucleotides are either available commercially or may be synthesized using methods described in the literature.

"Oligonucleotide" or "polynucleotide," which are used synonymously, means a linear polymer of natural or modified nucleosidic monomers linked by phosphodiester bonds or analogs thereof. The term "oligonucleotide" usually refers to a shorter polymer, e.g., comprising from about 3 to about 100 monomers, and the term "polynucleotide" usually refers to longer polymers, e.g., comprising from about 100 monomers to many thousands of monomers, e.g., 10,000 monomers, or more. Oligonucleotides comprising probes or primers usually have lengths in the range of from 12 to 60 nucleotides, and more usually, from 18 to 40 nucleotides. Oligonucleotides and polynucleotides may be natural or synthetic. Oligonucleotides and polynucleotides include deoxyribonucleosides, ribonucleosides, and non-natural analogs thereof, such as anomeric forms thereof, peptide nucleic acids (PNAs), and the like, provided that they are capable of specifically binding to a target genome by way of a regular pattern of monomer-to-monomer interactions, such as Watson-Crick type of base pairing, base stacking, Hoogsteen or reverse Hoogsteen types of base pairing, or the like.

Usually nucleosidic monomers are linked by phosphodiester bonds. Whenever an oligonucleotide is represented by a sequence of letters, such as "ATGCCTG," it will be understood that the nucleotides are in 5' to 3' order from left to right and that "A" denotes deoxyadenosine, "C" denotes deoxycytidine, "G" denotes deoxyguanosine, "T" denotes deoxythymidine, and "U" denotes the ribonucleoside, uridine, unless otherwise noted. Usually oligonucleotides comprise the four natural deoxynucleotides; however, they may also comprise ribonucleosides or non-natural nucleotide analogs. It is clear to those skilled in the art when oligonucleotides having natural or non-natural nucleotides may be employed in methods and processes described herein. For example, where processing by an enzyme is called for, usually oligonucleotides consisting solely of natural nucleotides are required. Likewise, where an enzyme has specific oligonucleotide or polynucleotide substrate requirements for activity, e.g., single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al., *Molecular Cloning,* Second Edition (Cold Spring Harbor Laboratory, New York, 1989), and like references. Oligonucleotides and polynucleotides may be single stranded or double stranded.

Oligonucleotides and polynucleotides may optionally include one or more non-standard nucleotide(s), nucleotide analog(s) and/or modified nucleotides. Examples of modified nucleotides include, but are not limited to diaminopurine, $S^2T$, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethY1-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethY1-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methY1-2-thiouracil, 2-thiouracil, 4-thiouracil, 5-methyluracil, uracil-5-oxyacetic acid methylester, uracil-5-oxyacetic acid (v), 5-methY1-2-thiouracil, 3-(3-amino-3-N-2-carboxypropyl)uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone.

"Oligonucleotide tag" or "tag" means an oligonucleotide that is attached to a polynucleotide and is used to identify and/or track the polynucleotide in a reaction. Usually, an oligonucleotide tag is attached to the 3'- or 5'-end of a polynucleotide to form a linear conjugate, sometime referred to herein as a "tagged polynucleotide," or equivalently, an "oligonucleotide tag-polynucleotide conjugate," or "tag-polynucleotide conjugate." Oligonucleotide tags may vary widely in size and compositions; the following references provide guidance for selecting sets of oligonucleotide tags appropriate for particular embodiments: Brenner, U.S. Pat. No. 5,635,400; Brenner et al., *Proc. Natl. Acad. Sci.,* 97: 1665; Shoemaker et al. (1996) *Nature Genetics,* 14:450; Morris et al., EP Patent Pub. 0799897A1; Wallace, U.S. Pat. No. 5,981,179; and the like.

In certain exemplary embodiments, a detectable label can be used to detect one or more molecules (e.g., a nucleotide, primer and/or target sequence) described herein. Examples of detectable markers include various radioactive moieties, enzymes, prosthetic groups, fluorescent markers, luminescent markers, bioluminescent markers, metal particles, protein-protein binding pairs, protein-antibody binding pairs and the like. Examples of fluorescent proteins include, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, dansyl chloride, phycoerythrin and the like. Examples of bioluminescent markers include, but are not limited to, luciferase (e.g., bacterial, firefly, click beetle and the like), luciferin, aequorin and the like. Examples of enzyme systems having visually detectable signals include, but are not limited to, galactosidases, glucorinidases, phosphatases, peroxidases, cholinesterases and the like. Identifiable markers also include radioactive compounds such as $^{125}I$, $^{35}S$, $^{14}C$, or $^{3}H$. Identifiable markers are commercially available from a variety of sources.

Fluorescent labels and their attachment to nucleotides and/or oligonucleotides are described in many reviews, including Haugland, *Handbook of Fluorescent Probes and Research Chemicals*, Ninth Edition (Molecular Probes, Inc., Eugene, 2002); Keller and Manak, DNA Probes, 2nd Edition (Stockton Press, New York, 1993); Eckstein, editor, *Oligonucleotides and Analogues: A Practical Approach* (IRL Press, Oxford, 1991); and Wetmur, *Critical Reviews in Biochemistry and Molecular Biology*, 26:227-259 (1991). Particular methodologies applicable to the invention are disclosed in the following sample of references: U.S. Pat. Nos. 4,757,141, 5,151,507 and 5,091,519. In one aspect, one or more fluorescent dyes are used as labels, e.g., as disclosed by U.S. Pat. Nos. 5,188,934 (4,7-dichlorofluorescein dyes); 5,366,860 (spectrally resolvable rhodamine dyes); 5,847,162 (4,7-dichlororhodamine dyes); 4,318,846 (ether-substituted fluorescein dyes); 5,800,996 (energy transfer dyes); Lee et al.; 5,066,580 (xanthine dyes); 5,688,648 (energy transfer dyes); and the like. Labelling can also be carried out with quantum dots, as disclosed in the following patents and patent publications: U.S. Pat. Nos. 6,322,901, 6,576,291, 6,423,551, 6,251,303, 6,319,426, 6,426,513, 6,444,143, 5,990,479, 6,207,392, 2002/0045045 and 2003/0017264. As used herein, the term "fluorescent label" includes a signaling moiety that conveys information through the fluorescent absorption and/or emission properties of one or more molecules. Such fluorescent properties include fluorescence intensity, fluorescence lifetime, emission spectrum characteristics, energy transfer, and the like.

"Polymorphism" or "genetic variant" means a substitution, inversion, insertion, or deletion of one or more nucleotides at a genetic locus, or a translocation of DNA from one genetic locus to another genetic locus. In one aspect, polymorphism means one of multiple alternative nucleotide sequences that may be present at a genetic locus of an individual and that may comprise a nucleotide substitution, insertion, or deletion with respect to other sequences at the same locus in the same individual, or other individuals within a population. An individual may be homozygous or heterozygous at a genetic locus; that is, an individual may have the same nucleotide sequence in both alleles, or have a different nucleotide sequence in each allele, respectively. In one aspect, insertions or deletions at a genetic locus comprises the addition or the absence of from 1 to 10 nucleotides at such locus, in comparison with the same locus in another individual of a population (or another allele in the same individual). Usually, insertions or deletions are with respect to a major allele at a locus within a population, e.g., an allele present in a population at a frequency of fifty percent or greater.

"Primer" includes an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. Usually primers are extended by a DNA polymerase. Primers usually have a length in the range of between 3 to 36 nucleotides, from 5 to 24 nucleotides, or from 14 to 36 nucleotides. In certain aspects, primers are universal primers or non-universal primers. Pairs of primers can flank a sequence of interest or a set of sequences of interest. Primers and probes can be degenerate in sequence. In certain aspects, primers bind adjacent to the target sequence, whether it is the sequence to be captured for analysis, or a tag that it to be copied.

"Solid support," "support," and "solid phase support" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. Microarrays usually comprise at least one planar solid phase support, such as a glass microscope slide. Semisolid supports and gel supports are also useful in the present invention, especially when polony amplification is used.

"Specific" or "specificity" in reference to the binding of one molecule to another molecule, such as a target sequence to a probe, means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecules in a reaction or sample, it forms the largest number of the complexes with the second molecule. In certain aspects, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak non-covalent chemical interactions, such as van der Waal forces, hydrogen bonding, base-stacking interactions, ionic and hydrophobic interactions, and the like, dominate the interaction of the molecules.

"$T_m$" is used in reference to "melting temperature." Melting temperature is the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation. $T_m$=81.5+0.41 (%

G+C), when a nucleic acid is in aqueous solution at 1 M NaCl (see e.g., Anderson and Young, "Quantitative Filter Hybridization," in *Nucleic Acid Hybridization* (1985). Other references (e.g., Allawi, H. T. & Santa Lucia, J., Jr., *Biochemistry* 36, 10581-94 (1997)) include alternative methods of computation which take structural and environmental, as well as sequence characteristics into account for the calculation of $T_m$.

In certain aspects, nucleic acid sequences derived or obtained from one or more organisms are provided. As used herein, the term "organism" includes, but is not limited to, a human, a non-human primate, a cow, a horse, a sheep, a goat, a pig, a dog, a cat, a rabbit, a mouse, a rat, a gerbil, a frog, a toad, a fish (e.g., Danio Rerio) a roundworm (e.g., *C. elegans*) and any transgenic species thereof. The term "organism" further includes, but is not limited to, a yeast (e.g., *S. cerevisiae*) cell, a yeast tetrad, a yeast colony, a bacterium, a bacterial colony, a virion, virosome, virus-like particle and/or cultures thereof, and the like.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references, patents and published patent applications cited throughout this application are hereby incorporated by reference in their entirety for all purposes.

The following examples are set forth as being representative of the present invention. These examples are not to be construed as limiting the scope of the invention as these and other equivalent embodiments will be apparent in view of the present disclosure, figures, tables, and accompanying claims.

EXAMPLE I

Use of Entangled Sequencing to Reveal Genetic Interactions

Figure 2:
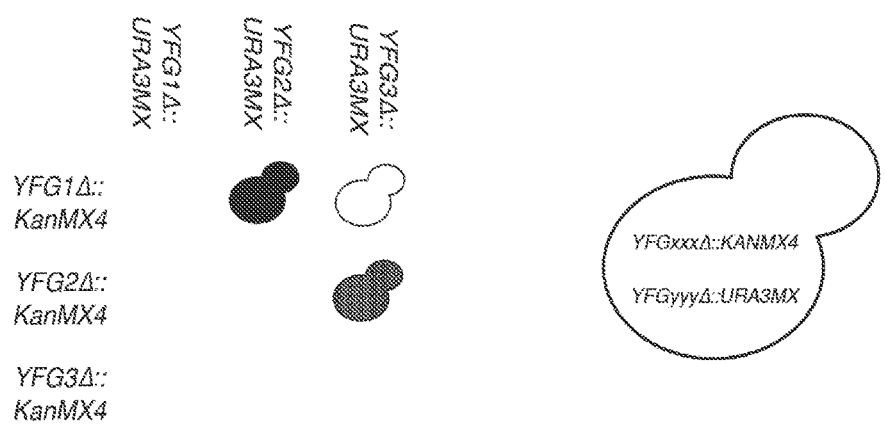
FIGS. 2A-2E schematically depict an overview of the barcode fusion genetics (BFG) strategy for genetic interaction mapping of the yeast Saccharomyces cerevisiae. A) A complex pool of double-mutant strains was efficiently generated from single-mutant yeast strain pools by crossing a pool of $Kan^R$ deletion strains with a pool of Ura+ deletion strains using the systematic genetic analysis (SGA) approach (Tong et al. (2001) Science; Tong et al. (2004) Science; Costanzo et al. (2010) Science). B) Strains in the double mutant pool were grown competitively, such that faster growing strains represented a greater fraction of the final population. C) A dilute suspension of double-mutant cells was used to generate a water-in-oil emulsion, such that each aqueous droplet contained either zero or one cell encapsulated together with PCR reagents. This was necessary to ensure that each barcode fusion represented a single double mutant cell. D) A fusion PCR reaction (also known as 'crossover PCR' or 'overlap-extension PCR') was carried out within the emulsion to 'stitch' together barcode (BC) sequences from two distinct loci to form a composite barcode. E) Each composite barcode thus uniquely identified a double-mutant strain. Each composite barcode also contained internal and flanking universal sequences that permitted primer-templated sequencing of one or more of the substituent barcodes.
Figure 2:
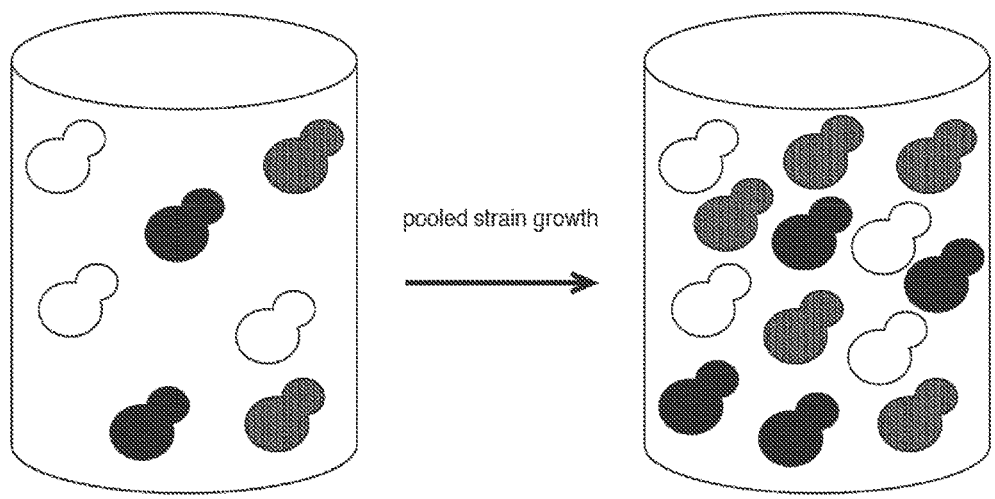
Figure 2:
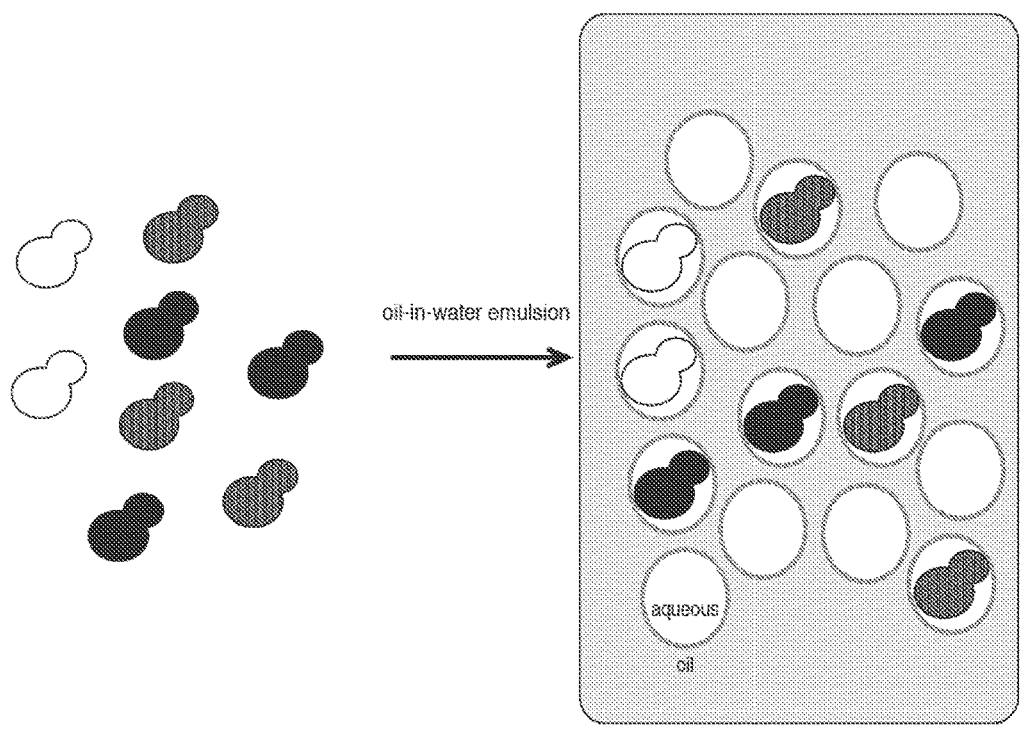
Figure 2:
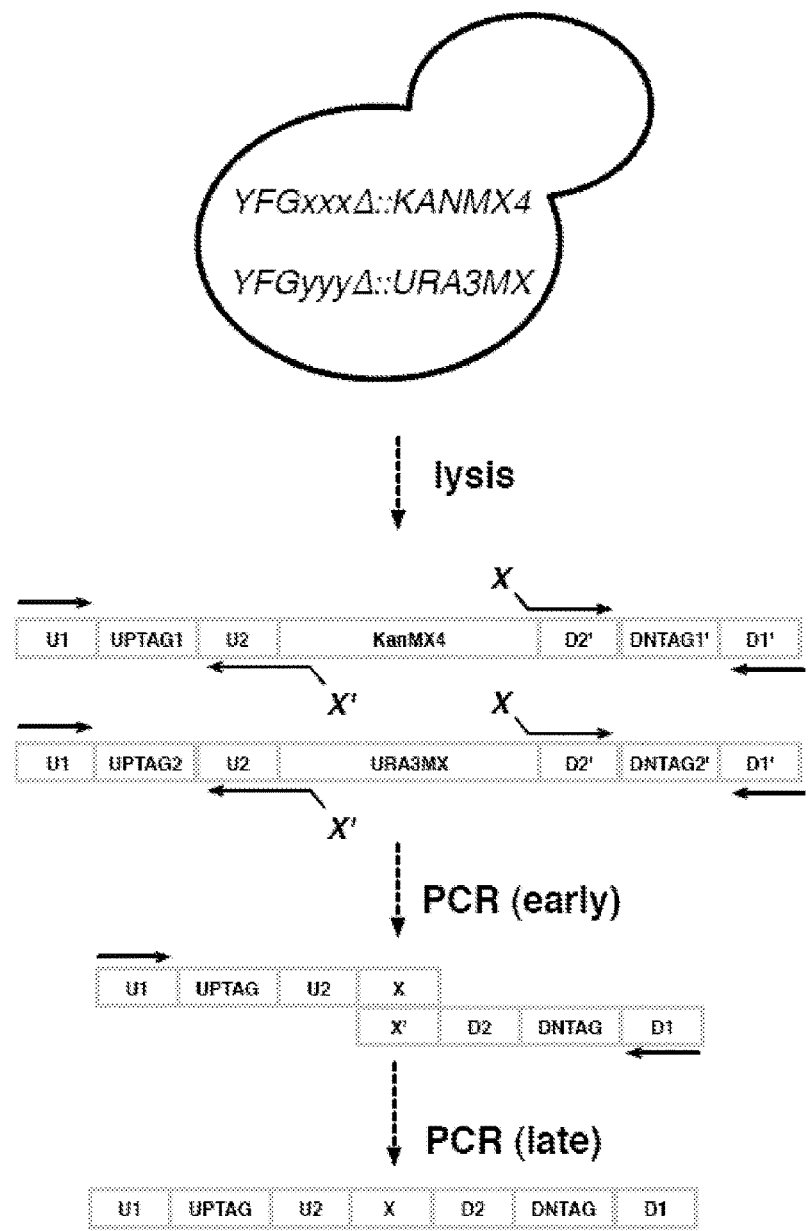
Figure 2:
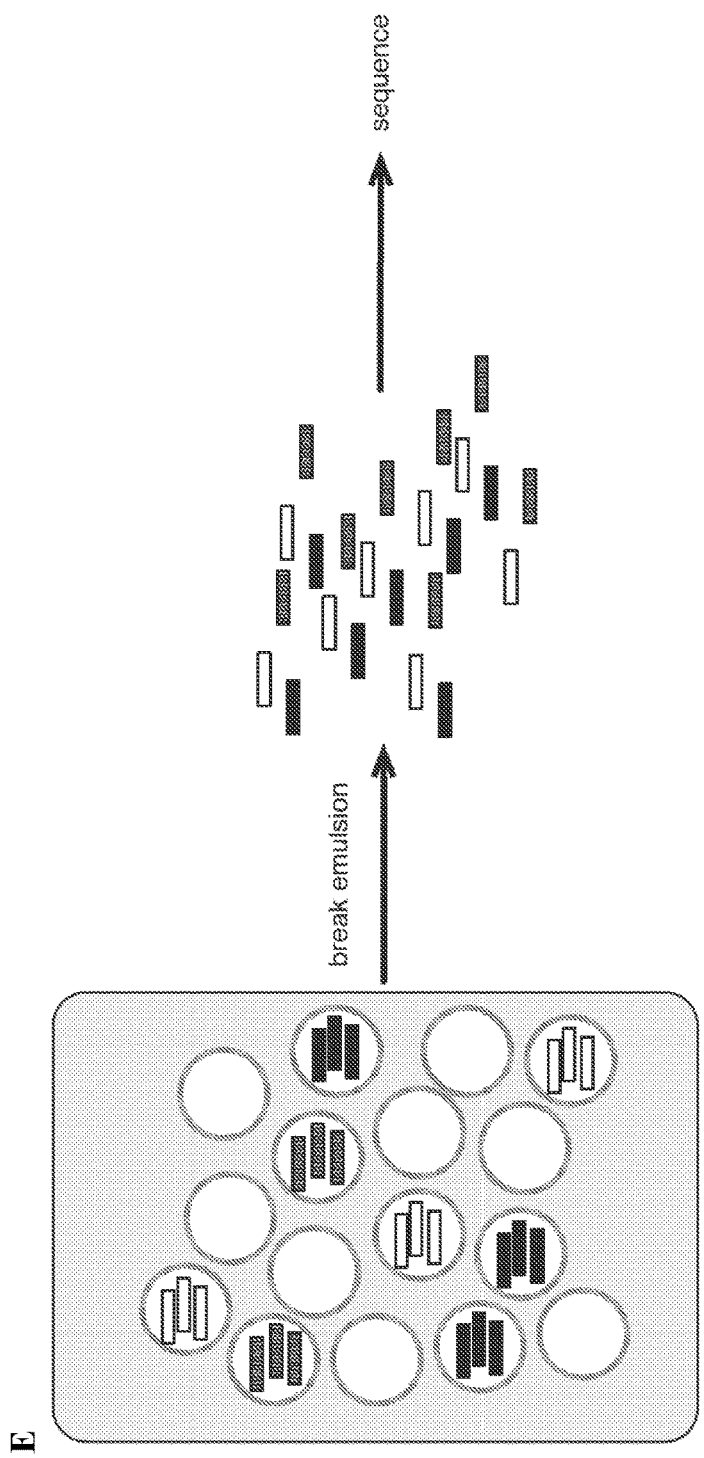

When two genes are perturbed simultaneously, a surprising phenotype sometimes emerges. Genetic interaction— defined by this phenomenon—suggests that the interacting genes have related functions. Genetic interactions have shaped current understanding of nearly all known biological pathways. Examples of genetic interaction encompass complex human diseases that require multiple mutations, such as cancer. Due to its facile genetics, *S. cerevisiae* remains a key model organism for the study of genetic interactions. Of particular value to studying genetic interactions is a collection of deletion strains corresponding to all non-essential yeast genes, in which the deleted gene has been replaced with a selectable marker flanked by two 'barcode' sequences that are specific to the deleted gene. A high-capacity methodology, barcode fusion genetics, has been developed that uses large-scale sequencing as a read-out to screen for tens of thousands of possible genetic interactions in single assay (See, e.g., U.S. Patent Application No. 2009/0098555 and FIG. 2). The efficient sequencing of pairs of barcodes in a complex mixture via second generation sequencing can be difficult, however. Sequencing of two regions (e.g., barcodes) of a single fragment typically requires either one very long read (i.e. capillary-based Sanger sequencing that is low-throughput) or two very short reads at double the time and sequencing cost.

Methods of entangled mate sequencing as described herein allow for the efficient sequencing and identification of pairs of barcode sequences within a complex mixture of library fragments. In studies thus far, approximately 2 million entangled reads have been obtained, of which approximately 1.5 million could be uniquely identified with a particular barcode pair known to be in a reference collection of fused barcodes. These 1.5 million identified fragments identified from a single lane on an Illumina GA2 sequencer represented approximately 7,000 unique types from the library. Examples of using entangled sequencing to read out results of the barcode fusion genetics ("BFG") strategy for genetic interaction mapping are depicted in Table 1. Barcodes corresponding to each gene pair have a unique predicted sequence pattern ("Predicted Sequence") which is mapped to observed sequences obtained by entangled mate sequencing of a fused barcode library on an Illumina GA2.

TABLE 1

| Gene 1 | Gene 2 | Predicted Sequence | Observed Sequence |
|--------|--------|--------------------|--------------------|
| YNG1 | SAC3 | SKWRYKRGWCWSSAYYM RSYSRKAW KMGAKRMM TYSKRGM (SEQ ID NO: 2) | SKWRYKRGMCWSSAYYM RSYSRKAWKMGAKRMM TYSKRGM (SEQ ID NO: 8) |
| YNG1 | CDC73 | SKWRMKRGKMYRCRTWM KCYSATMWKMGAKRMM TYSKRGM (SEQ ID NO: 3) | SKWRMKRGKMYRCRTWM KCYSATMWKAGAKRMM TYSKRGM (SEQ ID NO: 9) |
| SAC3 | YNG1 | SKWRSSAKSAKMKRYARK SARYSAMYMGAKRMM TYSKRGM (SEQ ID NO: 4) | SKWASSAKSAKMKRYARK SARYSAMYMGAKRMA TYSKRGM (SEQ ID NO: 10) |
| SUB1 | SWI1 | SKWRYKYWTMCWYWR MKSSSSWKGMTMGAKR MMTYSKRGM (SEQ ID NO: 5) | SKWRMGRGYMKRSAYWY KMTKMYMWKMGAKR MMTYSKRGM (SEQ ID NO: 11) |
| SWP82 | YNG1 | SKWRSSMTGAWMTRYMA KSMKWGWMKMGAKRMM TYSKRGM (SEQ ID NO: 6) | SKWRSSMTGAWMTRYMA KSMKWGWMKMGAKR MMTYSKRGM (SEQ ID NO: 12) |
| GBP2 | SAS4 | SKWRYRTMTTSSYSWWGK CSMMSMRKMGAKRMM TYSKRGM (SEQ ID NO: 7) | SKWRYRTMTTSSYSWWG KCSMMSMRKAGAKRMM TYSKRGM (SEQ ID NO: 13) |

A, adenine; C, cytosine; G, guanine; T, thymine; R, A or G; Y, C or T; S, G or C; W, A or T; K, G or T; M, A or C.

EXAMPLE II

BFG on a Strain Pool with Pair-Wise Combinations Among 74 Uniquely Barcoded Loci The results from a pilot experiment aimed at measuring genetic interaction amongst 74 genes involved in transcription elongation are described in this example. This experiment demonstrates quantitation of fused barcodes from a heterogeneous pool.

Genes with known or hypothesized relationships to transcription elongation were selected. For all 74 of these genes, URA3-replaced MATa haploid strains were derived from J. Boeke's 'Magic Marker' diploid strain collection. For 60 of the genes, the kanMX-replaced MATα strain was obtained from the YKO deletion collection. The presence of 14 of the strains in only the URA3-marked pool indicated that pair-wise combinations among these 14 strains should not be observed, thus providing a set of 91 (14 choose 2) negative control strains that permit assessment of the background rate at which barcodes from different cells are stitched together.

Figure 3:
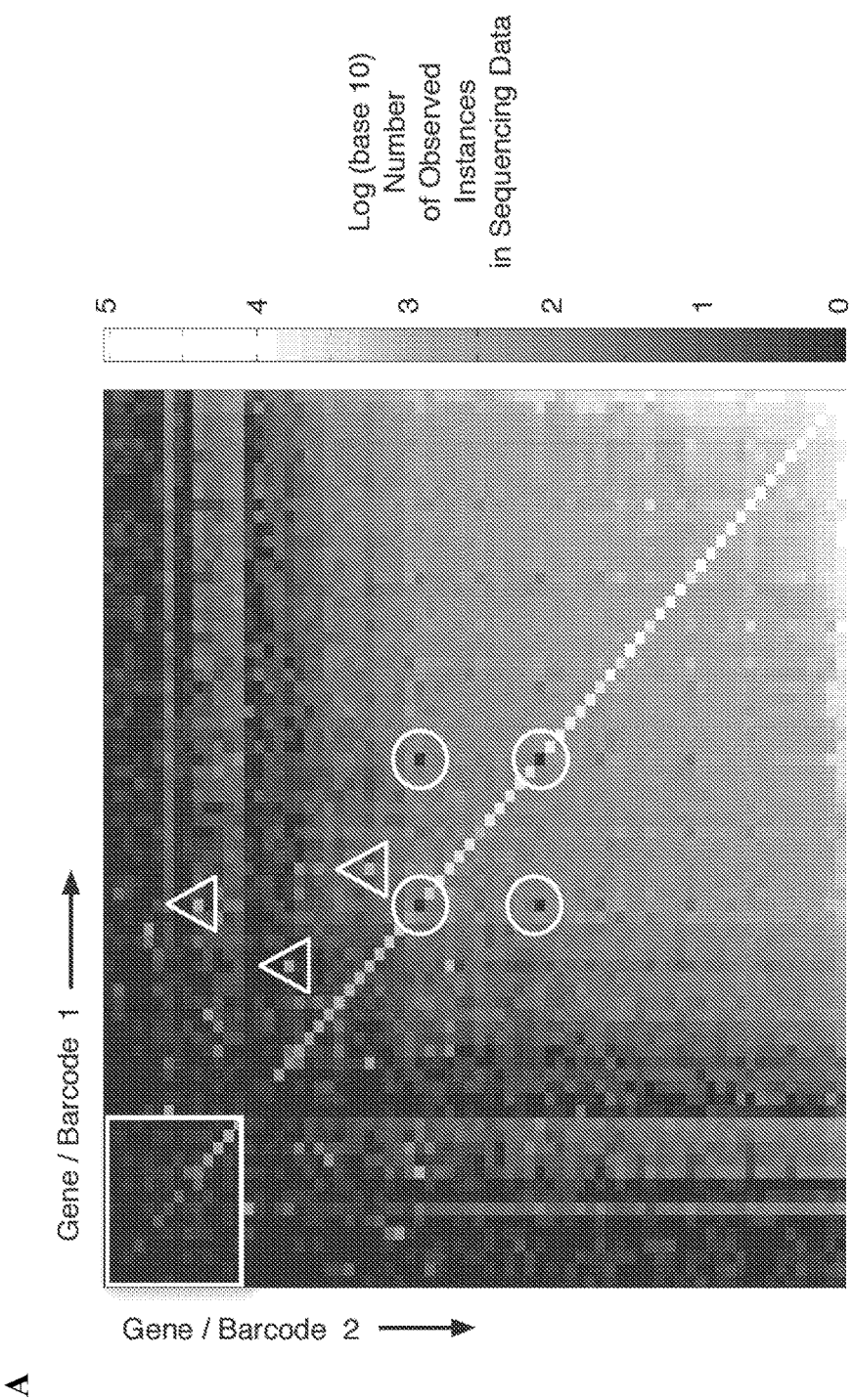
FIGS. 3A-3B graphically depict the number of observed counts for each fused-barcode tag from a "$t_0$" pool of all double mutants amongst 74 transcription elongation genes. A) A single Solexa GA2 lane produced 1.5 million mapable fusion-barcode sequences. 'Self-self' tags connecting up- and down-tags from the same gene are along the diagonal. Circles correspond to self-self tags expected to be absent given known problems with either the up- or down-tag. Certain circles show the expected absence of a fused barcode between two loci that each have known defective down-tags. A set of negative control gene pairs was present, in which no off diagonal counts were expected since deletions (and associated barcodes) for these genes were only present in one mating type. No such pair was observed to have greater than 10 fused barcode counts, indicating a low background of random stitching of barcodes present in different cells. Triangles show a few visually identified potential alleviating interactions—none have been previously tested for genetic interaction (they are being tested) one of which (ADA2/SAC3) corresponds to a known protein interaction. A few potential synergistic interactions were identified visually, which either agreed or disagreed with previous interaction data or have not been previously examined. Thus, 80% of the synergistic interactions identified that had been previously tested agreed with these findings. These results indicate that quantitation of doubly barcoded strains by the BFG method coupled with entangled mate sequencing can reveal the effects of selection within a complex heterogeneous strain pool. B) Genes/barcode legend for part A).

All haploid strains were pooled, selected for mated diploids, sporulated and selected for His$^+$ Mata haploids and for both barcode-linked markers. This pool was recovered for approximately six doublings in YPD and represents the 'time 0' ($t_0$) pool of double mutant cells which will be the starting point for subsequent selection experiments. An aliquot of this pool was subjected to the BFG emulsion/lysis/fusion-PCR process, and sequenced using a Solexa GA2 instrument. This yielded 1.5 million mappable fused barcodes. The results (FIG. 3) clearly indicate specific 'stitching' of barcodes arising from the same double mutant cell. Given that the $t_0$ pool had already undergone some competitive growth selection, an initial visual inspection already could identify some genetic interactions from the $t_0$ control (see FIG. 3). Importantly, the observed quantitation was achieved by entangled mate sequencing, by mapping entangled reads to a database of possible species of fused barcode.

EXAMPLE III

Computational Methods for Genomic Re-Sequencing Using Entangled Mate Sequencing One important application of entangled mate sequencing is to sequence a genome that has a known related genome (i.e., a reference genome), also known as re-sequencing. Efficient re-sequencing has great impact on many applications, including, but not limited to, discovering genetic variations in human populations, which permits the association of genes with diseases and other phenotypes and therefore is important to personalized medicine.

The re-sequencing task utilizes computational approaches described herein to handle the new challenges arising from entangled mate sequencing. For example, the fact that each pair of the entangled bases in a read comes from two locations of the genome separated by an unknown distance complicates the process of mapping each read onto the reference genome.

In this example, a computational pipeline that solves these problems is described. This pipeline enabled the assembly of entangled reads with the aid of a reference genome. Specifically, the pipeline was able to map entangled reads onto the given reference genome and successfully assemble the mapped reads into contiguous regions that covered 99.9% of the reference genome.

The pipeline can be divided into three stages (FIG. 3): (1) calling entangled bases from raw signal; (2) mapping entangled reads to the reference genome; and (3) assembling mapped reads into contiguous consensus sequences.

Base Calling

In the first stage, the pipeline takes raw signals generated by the Illumina Sequencer and converts them into a sequence of entangled bases. One way to do this was to first take the raw intensity signals from the four channels of Illumina Sequencer, correct them for cross-talk noise, and then call the bases using channel-specific intensity thresholds. In one preliminary experiment where a library of entangled barcodes was sequenced, the bases were able to be called and more than 50% of the resulting reads were mapped back to the reference collection of nucleic acid sequences. This is comparable to previous reports that used the standard Illumina base-caller to map non-entangled reads from the PhiX174 genome, in which less than 40% could be mapped to the reference genome without any mismatches (Kircher (2009) Genome Res. 10:R83).

Another way to perform base calling was to take the raw intensity signals, correct them for cross-talk and phasing noises, and then cluster the resulting 4-dimension vectors of intensities by fitting a Gaussian mixture model algorithmically, where each mixture component corresponds to one of 16 possible pairs of entangled nucleotide bases. Each intensity vector was then 'called' to be the entangled base corresponding to the maximum-likelihood component. A Phred-style quality score was computed by converting the probability that the intensity vector belongs to its assigned Gaussian mixture component. In one preliminary experiment where a library of several million reads with each read containing the entangled information of two distinct 20-bp DNA tags was sequenced, 75% of the reads were mapped from each lane, as compared with un-entangled mate-pair reads for the same library in which 70-80% of reads are mappable. At a Phred threshold of 10, the estimated error rate was 2.5%, close to the range of typical Illumina sequencing errors at the same confidence level. At higher Phred-like cutoffs, the error rate can be lowered to 1-1.5%. High performance of base-calling was been achieved as measured in terms of the fraction of mappable reads and error-rate on mapped reads.

Mapping Entangled Reads

In the second stage, the entangled reads called in the first stage were mapped onto the reference genome. In analogy with previous procedures (e.g., BLAST) for aligning a particular conventional (non-entangled) query sequence with a library or database of conventional sequences, the process a) generates a list of 'seed alignments' using a rapid lookup procedure (word lookup); b) attempts to extend seed alignments without the introduction of gaps (un-gapped extension); and c) attempts to refine and extend a subset of alignments from (b), this time allowing gaps in the alignment.

There are at least two methods to carry out this procedure. In the first way, DNA libraries will be constructed such that each read will begin with a known, constant "runway" sequence of length k entangled with k unknown bases. Thus, each of the first k entangled bases can be readily disentangled. The resulting k-mers will then be looked up in the reference collection of nucleic acid sequences for exact matches, generating a list of seed alignments. Possible locations for a read will be narrowed down quickly using a hash table storing all k-mers in the reference sequence and their locations. For each seed alignment, alignment will be attempted by comparing subsequent bases on the reference sequence with entangled bases on the read to examine if they are compatible. Next, a subset of alignments will be refined by attempting gapped extension. After finishing the previous steps, albeit will be possible to map half of an entangled read to the reference sequence and simultaneously disentangle the read to retrieve the other half, which can be used to map to the reference sequence directly. The length of a runway sequence will be decided by a number of factors, including, but not limited to, reference genome size and read length. For example, for a genome of 5 Mbp, a mappable read requires, on average, 9.5 attempts if a runway sequence of 9 bases is used.

Figure 4:
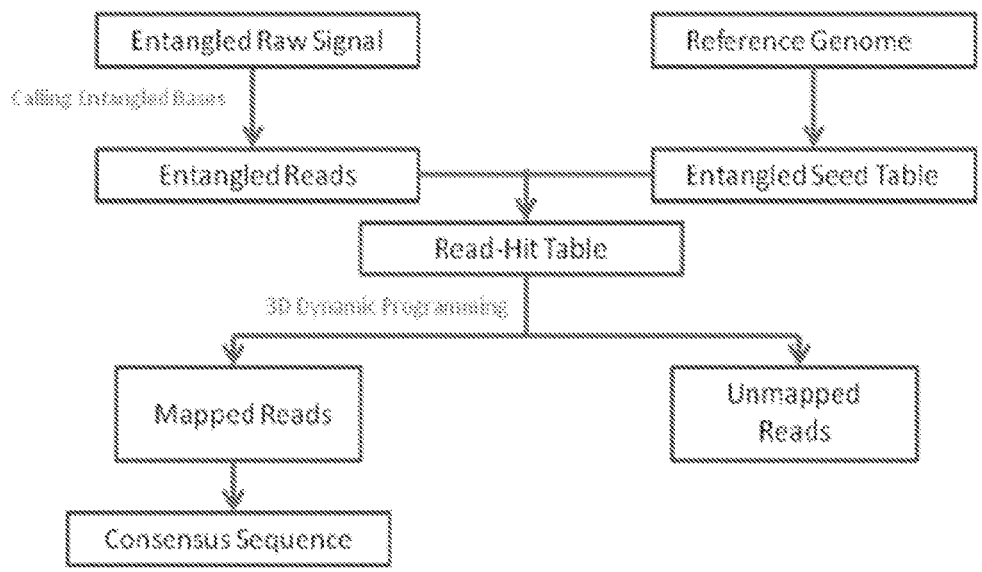
FIG. 4 depicts a flowchart for assembling contiguous consensus sequences using a reference genome as template.
Figure 5:
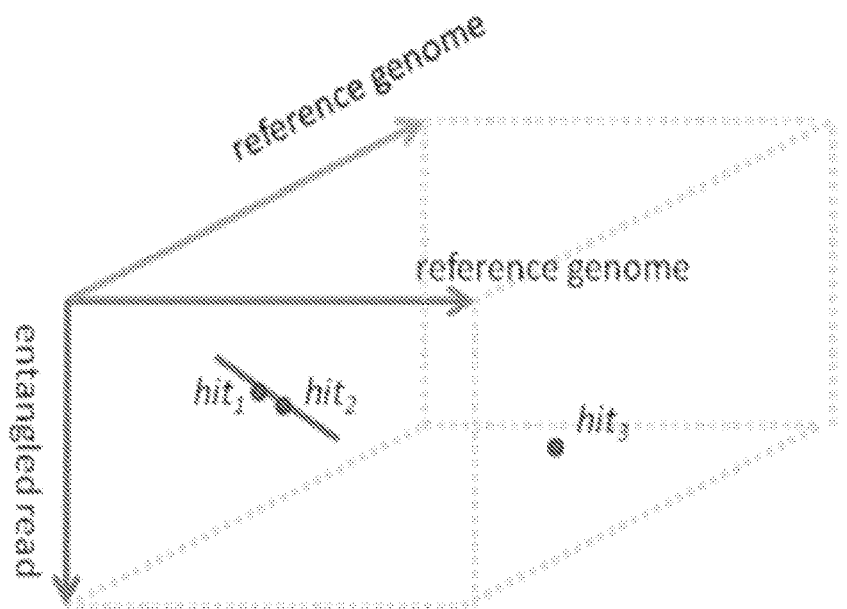
FIG. 5 schematically depicts a dynamic programming approach for performing an optimal local alignment of an entangled read simultaneously to two source loci within the reference genome.

In the second method, DNA construct libraries did not have runway sequences. Possible locations for a read were narrowed down quickly using a hash table (e.g., an entangled seed table), which is constructed differently from the first method. The table was constructed by entangling pairs of short sequences (seeds) on pairs of locations on the reference genome. The table stored the entangled seeds and the corresponding pairs of locations. The length of the seeds was determined by a number of factors, including the size of the reference genome and the tradeoff between sensitivity and efficiency. The distance between two seeds was constrained by the DNA fragment size. The range of the distance could be empirically estimated from the library preparation. Given an entangled read, a list of candidate location pairs could be determined by scanning all n-mers of the read, where n is equal to the seed length, and looking each one up in the entangled seed table. With the list of candidate locations, step (b) of the pipeline determined the best un-gapped alignment between a read and two stretches of the reference genome. Starting from the matched seeds, the following entangled bases were compared with the corresponding bases at the candidate locations on the reference genome, and the entangled sequence was aligned simultaneously with two genomic locations (FIG. 4). This process was continued until the whole read was able to be aligned, or until there were too many mismatches, at which time step (c), a gapped extension was performed for a subset of alignments from step (b). Step (c) was accomplished by solving a "3D Dynamic Programming" problem, in which one dimension is the entangled sequence and two additional dimensions represent two genomic regions to which the two component sequences making up the entangled sequence are expected to map (FIG. 5).

After stage two, the list of the entangled reads that could be aligned with the reference genome was determined and used to assemble a collection of consensus sequences from the target genome.

Generate Consensus Sequences

In the third stage, the mapped reads were stacked over the reference genome, and a consensus base was derived by selecting the base represented by the majority of reads at each position. Sets of contiguous consensus bases represent a consensus sequence.

Simulation Results

The pipeline was tested using entangled reads simulated from real paired-end reads. The reads were generated by computationally entangled 36 base pair paired-end Illumina reads from a *Salmonella* strain. Greater than 80% of the 8 million entangled reads were successfully mapped to the *Salmonella* reference genome. The resulting consensus sequence covered 99.9% of the reference genome, and the average read depth was approximately 100. As a comparison, MAQ, a read mapper for non-entangled reads, was able to map approximately 88% of the paired-end reads, and the resulting consensus genome had lower coverage.

EXAMPLE IV

Methods for Producing DNA Libraries for Entangled Mate Sequencing

The basic material requirement for using entangled mate sequencing is a library of template DNA molecules in which each molecule has at least two sequence regions of interest flanked at the 5' end by universal, library-wide primer binding sites. In various embodiments, the primer binding sites on each molecule can be different or the same, and have variable distance from their 3' end to the beginning of the DNA template sequence region of interest.

In certain exemplary embodiments, preparation methods that are used to synthesize template libraries that are capable of facilitating entangled sequencing are provided. Two strategies are outlined below.

1. Random Tandem Entangled Mate Sequencing Library

Figure 6:
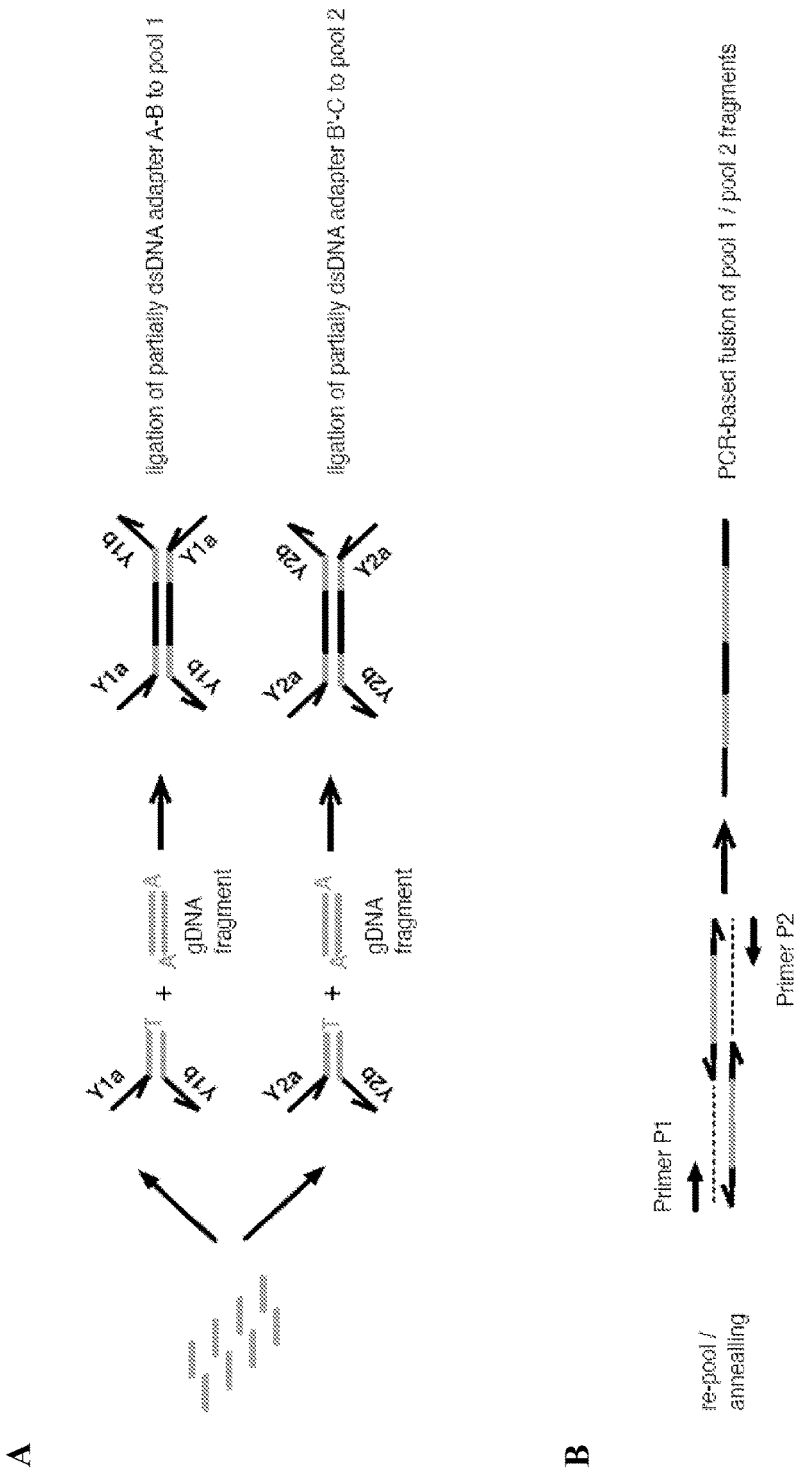
FIGS. 6A-6B depict a scheme used to fuse two random genomic fragments for entangled sequencing.

The first strategy connects two random genomic fragments with an intervening connector of known sequence that can act as priming site. In this way, two sequencing reactions can be simultaneously primed on the same strand, thus entangling two reads. The construction strategy is described in FIG. 6. Briefly, two pools (pool 1 and pool 2) of fragmented genomic (or other) DNA having approximately known length(s) are adapted via ligation by T4 DNA ligase under standard conditions (10-fold molar excess of adapter) with a corresponding pair of pool-specific partially double-stranded DNA adapters (AB and B'C). As depicted in FIG. 6, the adapters are designed such that sequence B contains the reverse complement of the sequence B'. After ligation, the pools are then combined and amplified with a set of primers that complementary to the single-strand parts of A and C. In this way, the resulting product contains a random fusion of template fragments from the original two pools, flanked by sequences A and C. Entangled sequencing of the library is performed using sequencing primers complementary to A and B.

2. Nested Mate-pair Entangled Sequencing Library

Figure 7:
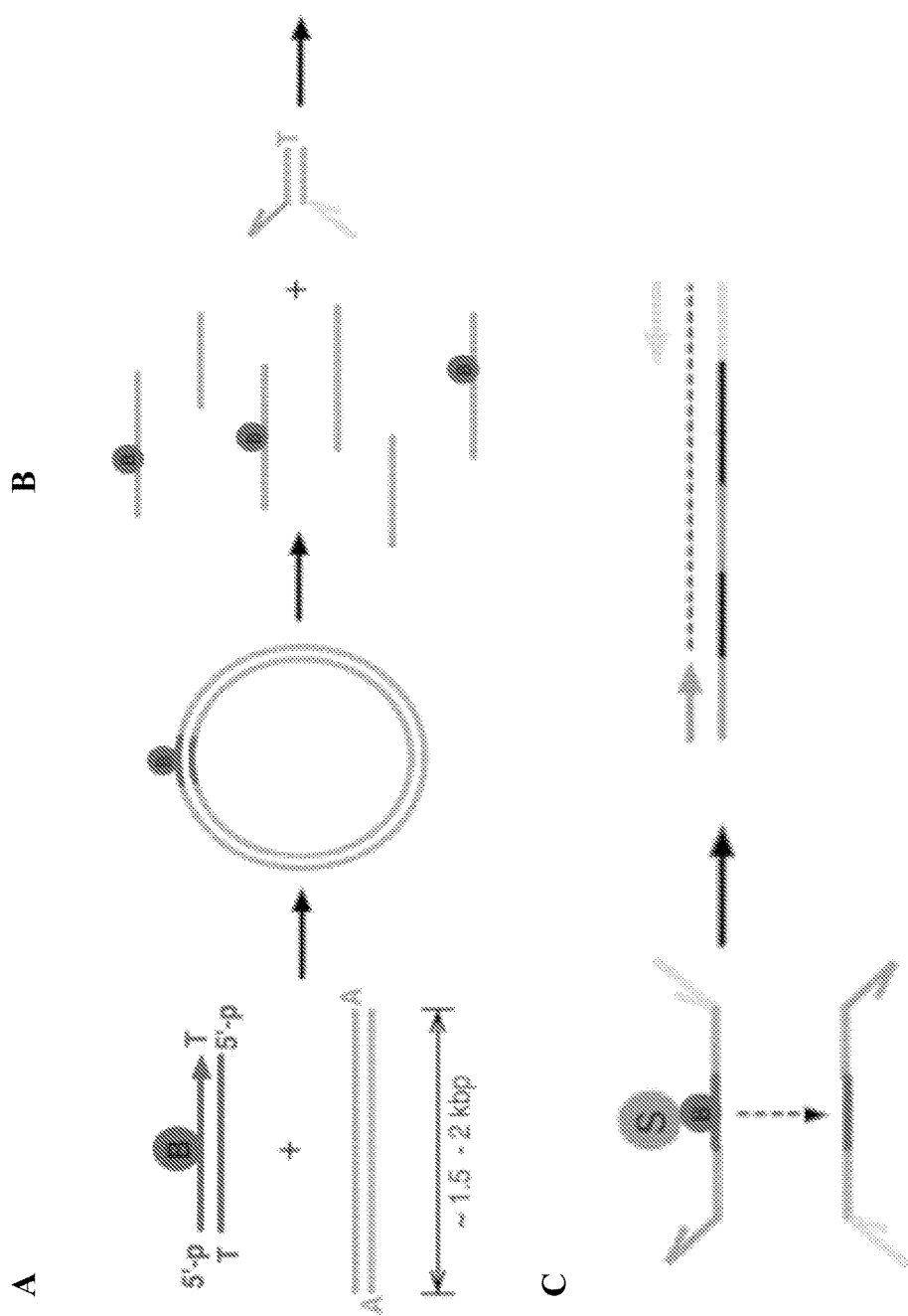
FIGS. 7A-7C depict a scheme for constructing a database of sequence signatures in which two entangled reads can be derived from the same single, long genomic fragment, providing sequence information from four loci with nested distance constraints. A) Circularization of genomic fragments via an internally biotinylated linker. B) Ligation of partially dsDNA adapter to re-sheared library (500-600 bp). C) Binding of internally biotinylated mate-paired fragments and release of unbiotinylated strand.

One strategy for genome sequencing is to perform sequencing by a combination of methods, with some sequencing of shorter fragments (e.g., using the Solexa method) and some sequencing of paired ends from longer fragments (e.g., using Sanger and/or 454 methods). Short-read sequencing provides economical depth of coverage, while paired-end or complete sequencing of longer-fragments facilitates assembly of fragments despite long repetitive elements. This example provides a novel strategy (FIG. 7) that can be used to obtain economical, short-read sequencing while providing longer distance constraints.

"Solexa sequencing" refers to a sequencing technology based on reversible dye-terminators. DNA molecules are first attached to primers on a slide and amplified so that local clonal colonies are formed (i.e., bridge amplification). One type of nucleotide at a time is then added, and non-incorporated nucleotides are washed away. The DNA can only be extended one nucleotide at a time. A camera takes images of the fluorescently labeled nucleotides and the dye is chemically removed from the DNA, allowing a next cycle.)

"454 sequencing" refers to a parallelized version of pyrosequencing was developed by 454 Life Sciences. The method amplifies DNA inside water droplets in an oil solution (emulsion PCR), with each droplet containing a single DNA template attached to a single primer-coated bead that then forms a clonal colony. The sequencing machine contains many picoliter-volume wells each containing a single bead and sequencing enzymes. Pyrosequencing uses luciferase to generate light for detection of the individual nucleotides added to the nascent DNA, and the combined data are used to generate sequence readouts.

"Sanger sequencing" refers to a chain-termination method that requires a single-stranded DNA template, a DNA primer, a DNA polymerase, radioactively or fluorescently labeled nucleotides, and modified nucleotides that terminate DNA strand elongation. The DNA sample is divided into four separate sequencing reactions, containing all four of the standard deoxynucleotides (dATP, dGTP, dCTP and dTTP) and the DNA polymerase. To each reaction is added only one of four dideoxynucleotides (ddATP, ddGTP, ddCTP, or ddTTP) which are the chain-terminating nucleotides, lacking a 3'-OH group required for the formation of a phosphodiester bond between two nucleotides, thus terminating DNA strand extension and resulting in DNA fragments of varying length.

A pool of genomic DNA is fragmented into long (e.g., 1.5-2.0 kilobase pair) fragments and circularized by means of a T-linker (FIG. 7, green) that is internally biotinylated on one strand. The resulting circularized genomic library is then fragmented into short (e.g., approximately 400 base pair) fragments, which are in turn ligated with a greater than 100-fold excess of partially double stranded (ds) DNA Y-adapter. Biotinylated fragments are isolated via pull-down with streptavidin-coated magnetic microbeads, and treated with sodium hydroxide to release the non-biotinylated strand. The single stranded (ss) DNA retained on the microbeads is then released and re-amplified with outer priming sequences.

EXAMPLE V

Identification of Sequence from Genomic Random Tandem Libraries Using Entangled Mate Sequencing A library of *Salmonella typhi* LT2 genomic DNA was sequenced using the random tandem method of fragment library construction. A pool of genomic DNA was harvested from 5 mL of overnight bacterial culture with phenol:chloroform extraction. Five micrograms of the isolated DNA was then subjected to shearing on a Covaris S2 Adaptive Acoustic System, with settings corresponding to a targeted DNA fragment size distribution of 200 bp (10% duty cycle, intensity setting 5, 200 cycles/burst, 180 seconds). The resulting fragmented library was then end-polished (End-It, Epicentre Biotech.) and 3'-adenylated (Klenow exo-, NEB), cleaned up and eluted in 50 µL of Tris HCl pH 8.0 (Qiaquick PCR Purification Kit, Qiagen).

The DNA library was then split into two equal-sized aliquot pools (Pool 1 and Pool 2), and 10 µL of each pool was then ligated to a specific corresponding partially-ds-DNA adapter, under conditions of 10-fold molar excess of adapter, for 15 minutes at 25 C (Ultrapure DNA Ligase, Enzymatics Inc). Specifically, Pool 1 was ligated to adapter Y1, and Pool 2 was ligated to adapter Y2. Adapter Y1 is a partially-dsDNA adapter created by annealing two 200 µM stock solutions of two HPLC-purified oligonucleotides (IDT): Y1-a (5'-ACACTCTTTCCCTACACGACGCTCT-TCCGATCT) (SEQ ID NO:14) and Y1-b (5'-phos-GATCG-GAAGAGCGCGTCAGTCACCGGAGCCAC) (SEQ ID NO:15). The sequences of Y1-a and Y1-b were designed such that 13 bp at the 3' end of Y1-a were complementary to 13 bp at the 5' end of Y1-b. Adapter Y2 was another partially dsDNA adapter, created by annealing two 200 µM stock solutions of two HPLC-purified oligonucleotides (IDT): Y2-a (5'-GAGCCGTAAGGACGACTTGGAT-GCTGGAC CTGT) (SEQ ID NO:16) and Y2-b (5'-phos-CAGGTCCAGCATCGTGGCT CCGGTGACTGACG) (SEQ ID NO:17). The sequences of Y2-a and Y2-b were designed such that 13 bp at the 3' end of Y2-a were complementary to 13 bp at the 5' end of Y2-b. Furthermore, the terminal 3' sequence of oligonucleotide Y2-b was designed to be reverse-complementary to the terminal 3' sequence of oligonucleotide Y1-b.

The ligated product mixtures from the Pool 1 and Pool 2 ligations were cleaned (Qiaquick) and then run separately on a 2% pre-stained gel (E-Gel SizeSelect 2%, Invitrogen), and a band of approximately 250 bp was collected from the gel into 25 µL of PCR-grade water (to remove unligated adapters). The purified ligation products from Pool 1 and Pool 2 were then combined, along with 50 µL of 2× Phusion HF Master Mix (Finnzymes), and this mixture was subjected to polymerase chain reaction with primers P1 and P2 that corresponded to sequences of Y1-a and Y2-a (P1: 5'-AAT-GATACGGCGACCACCGAGATCTACACTCTTTC-CCTACACGACGCTCTTCC GATCT (SEQ ID NO:18), P2: 5'-CAAGCAGAAGACGGCATACGAGATGAGCCGT AAGGACGACTTGG) (SEQ ID NO:19). The amplification of the mixture of Pool 1 and Pool 2 by primers P1 and P2 was promoted by annealing and templated extension of fragments from the two libraries via reverse-complementary sequences at the ends of Y1-b and Y2-b. The amplification via PCR was performed using the following thermal cycling program: (1) 5 minutes at 95 C, (2) 15 cycles of: 95 C for 30 sec, 55 C for 30 sec, 72 C for 1 min, and (3) 2 min at 72 C. This reaction was cleaned (Qiaquick) and run on a pre-stained 2% gel, and a band of approximately 500 bp was extracted into PCR-grade water. Sequencing by PCR-product cloning into a blunt-ended vector kit and bacterial host (Ultra-Blunt Cloning Kit, Stratagene) confirmed that the PCR product consisted of tandem fragments of *Salmonella* genomic DNA flanked by ligated adapters Y1 and Y2 and flanking PCR primer sequences P1 and P2. The final library fragments each had the sequence (5'-AATGATACGGC-GACCACCGAGATCTACACTCTTTCCCTACACG ACGCTCTTCCGATCT-X1-AGATCG-GAAGAGCGCGTCAGTCACCGGAGCCACG ATGCTG-GACCTGT-X2-AAAGGTCCAGCATCCAAGTCGTCCT-TACGGCTCATC TCGTATGCCGTCTTCTGCTTG) (SEQ ID NO:20) where X1 and X2 represent fragments from the original genomic pools Pool 1 and Pool 2.

This library was then sequenced using an Illumina GAII sequencer with a mixture of two sequencing primers Rand-Tand-1 (5' TCT ACA CTC TTT CCC TAC ACG ACG CTC TTC CGA TCT) (SEQ ID NO:21) and RandTand-2 (5' GAA GAG CGC GTC AGT CAC CGG AGC CAC GAT GCT GG) (SEQ ID NO:22). RandTand-1 and RandTand-2 are designed to anneal to sequences directly 5' of the two genomic fragments originating from Pool 1 and Pool 2, respectively. Sequencing resulted in approximately 8 million raw reads obtained on the Illumina instrument, with each read consisting of entangled sequence generated from priming by RandTand-1 and RandTand-2. Each read consisted of 40 called 'entangled' bases.

Approximately 1.2 million (15%) were mappable to the *Salmonella typhi* LT2 genome, allowing for two or fewer errors per read. Mapping was aided by the use of a six-base runway sequence immediately 3' from the priming sequence RandTand-2 (5'-ACCTGT). Unentangling of the first six entangled bases relied on the fact that the unknown sequence from sequence X1 was entangled with the runway sequence at the first six nucleotides.

What is claimed is:

1. A method of determining nucleotide sequence identities of heterogeneous, tethered nucleic acid template sequences comprising the steps of:
providing a mosaic target nucleic acid sequence including a first template nucleic acid sequence and a second template nucleic acid sequence, wherein the first and second template nucleic acid sequences are tethered and heterogeneous and of relatively homogeneous length;
simultaneously reading the first template nucleic acid sequence and the second template nucleic acid sequence to obtain a mixed entangled sequencing signal representative of each of the first template nucleic acid sequence and the second template nucleic acid sequence; and
disentangling the mixed sequencing signal into its constituent individual template sequences by matching the mixed entangled sequencing signal to its closest match in a reference collection of known sequence signatures wherein the mixed entangled sequencing signal is obtained by annealing a first primer sequence to a portion of the first template nucleic acid sequence and a second primer sequence to a portion of the second template nucleic acid sequence;
extending the annealed primers simultaneously; and
sequentially determining the identity of each set of two bases extended from the 3' ends of the first and second primers to obtain mixed base signatures and using said mixed base signatures to obtain a mixed nucleic acid sequence signature of the tethered first and second template nucleic acid sequences, wherein the identity of each set of two bases extended from the 3' ends of the first and second primers is sequentially determined by nucleotide addition sequencing.

2. The method of claim 1, wherein the heterogeneous, tethered nucleic acid template sequences represent one or more of a genome, a proteome, a transcriptome or a cellular pathway.

3. A method of determining nucleotide sequence identities of tethered, heterogeneous nucleic acid template sequences comprising the steps of:
providing a heterogeneous library of mosaic target nucleic acid sequences, in which a plurality include a first template nucleic acid sequence and a second template nucleic acid sequence, wherein the first and second template nucleic acid sequences are tethered and heterogeneous and of relatively homogeneous length;
simultaneously reading the first template nucleic acid sequence and the second template nucleic acid sequence to obtain a mixed entangled sequencing signal representative of each of the first template nucleic acid sequence and the second template nucleic acid sequence; and
disentangling the mixed sequencing signal into its constituent individual template sequences by matching the mixed entangled sequencing signal to its closest match in a reference collection of known sequence signatures wherein the mixed entangled sequencing signal is obtained by annealing a first primer sequence to a portion of the first template nucleic acid sequence and a second primer sequence to a portion of the second template nucleic acid sequence;
extending the annealed primers simultaneously; and
sequentially determining the identity of each set of two bases extended from the 3' ends of the first and second primers to obtain mixed base signatures and using said mixed base signatures to obtain a mixed nucleic acid sequence signature of the tethered first and second template nucleic acid sequences, wherein the identity of each set of two bases extended from the 3' ends of the first and second primers is sequentially determined by nucleotide addition sequencing.

4. The method of claim 3, wherein the first template nucleic acid sequence is a barcode sequence and the second template nucleic acid sequence is a genomic sequence.

5. The method of claim 3, wherein the reference collection is in a database.

6. The method of claim 3, wherein the plurality includes the first template nucleic acid sequence, the second template nucleic acid sequence, and a third template nucleic acid sequence wherein the first, second and third template nucleic acid sequences are tethered and heterogeneous and of relatively homogeneous length;
  simultaneously reading the first template nucleic acid sequence, the second template nucleic acid sequence and the third template nucleic acid sequence to obtain a mixed entangled sequencing signal representative of each of the first template nucleic acid sequence the second template nucleic acid sequence and the third template nucleic acid sequence; and
  disentangling the mixed sequencing signal into its constituent individual template sequences by matching the mixed entangled sequencing signal to its closest match in a reference collection of known sequence signatures.

7. The method of claim 3, wherein the mosaic target nucleic acid sequence includes 3 or more tethered, nucleic acid sequences.

8. The method of claim 3, wherein the mosaic target nucleic acid sequence is present on an array.

9. A method of determining nucleotide sequence identities of two tethered nucleic acid sequences comprising the steps of:
  providing a heterogeneous library of mosaic target nucleic acid sequences, in which a plurality include a first template nucleic acid sequence and a second template nucleic acid sequence, wherein the first and second template nucleic acid sequences are tethered and heterogeneous and of relatively homogeneous length;
  simultaneously reading the first template nucleic acid sequence, the second template nucleic acid sequence and the third template nucleic acid sequence to obtain a mixed entangled sequencing signal representative of each of the first template nucleic acid sequence the second template nucleic acid sequence and the third template nucleic acid sequence; and
  disentangling the mixed sequencing signal into its constituent individual template sequences by matching the mixed entangled sequencing signal to its closest match in a reference collection of known sequence signatures
  wherein the mixed entangled sequencing signal is obtained by annealing a first primer sequence to a portion of the first template nucleic acid sequence and a second primer sequence to a portion of the second template nucleic acid sequence;
  extending the annealed primers simultaneously; and
  sequentially determining the identity of each set of two bases extended from the 3' ends of the first and second primers to obtain mixed base signatures and using said mixed base signatures to obtain a mixed nucleic acid sequence signature of the tethered first and second template nucleic acid sequences, wherein the identity of each set of two bases extended from the 3' ends of the first and second primers is sequentially determined by nucleotide addition sequencing.

10. The method of claim 9, wherein the reference collection is a collection of sequence signatures and the second nucleic acid sequence is not present in the reference collection of sequence signatures.

11. The method of claim 9, wherein each mixed base signature sequence includes a set of two bases selected from the group consisting of AA, CC, GG, TT, AC, AG, AT, CG, CT and GT.

12. The method of claim 9, wherein the first and second template nucleic acid sequences are barcode sequences.

13. The method of claim 9, wherein the first and second template nucleic acid sequences are genomic sequences.

14. The method of claim 9, wherein the first and second primer sequences have the same sequence identity.

15. The method of claim 9, wherein the first and second primer sequences have a different sequence identity.

16. A method of identifying a cell having heterogeneous nucleic acid sequences comprising the steps of:
  providing a cell having a mosaic target nucleic acid sequence including a first barcode sequence and a second barcode sequence, wherein the first and second barcode sequences are tethered and heterogeneous and of relatively homogeneous length;
  simultaneously reading the first barcode sequence and the second barcode sequence to obtain a mixed entangled sequencing signal representative of each of the first barcode sequence and second barcode sequence;
  disentangling the mixed sequencing signal into its constituent individual barcode sequences by matching the mixed entangled sequencing signal to its closest match in a reference collection of known sequence signatures;
  wherein the mixed entangled sequencing signal is obtained by annealing a first primer sequence to a portion of the first template nucleic acid sequence and a second primer sequence to a portion of the second template nucleic acid sequence;
  extending the annealed primers simultaneously;
  sequentially determining the identity of each set of two bases extended from the 3' ends of the first and second primers to obtain mixed base signatures and using said mixed base signatures to obtain a mixed nucleic acid sequence signature of the tethered first and second template nucleic acid sequences, wherein the identity of each set of two bases extended from the 3' ends of the first and second primers is sequentially determined by nucleotide addition sequencing; and
  determining the nucleotide sequence identity of one or both of the tethered first and second barcode sequences to identify the cell from the mixed nucleic acid barcode sequence signature.

17. The method of claim 16, wherein the cell is a yeast cell.

18. The method of claim 17, wherein the yeast cell contains two or more alterations.

19. The method of claim 16, wherein the heterogeneous nucleic acid sequences represent one or more of a genome, a proteome, a transcriptome or a cellular pathway.

20. The method of claim 16, wherein the heterogeneous nucleic acid sequences represent *Homo sapiens* nucleic acid sequences.

21. The method of claim 1, wherein the step of determining the sequence is performed by comparing the nucleic acid sequence signature to a reference collection of seed sequences.

* * * * *